(12) United States Patent
Kam et al.

(10) Patent No.: US 7,109,459 B2
(45) Date of Patent: Sep. 19, 2006

(54) AUTO-FOCUSING METHOD AND DEVICE FOR USE WITH OPTICAL MICROSCOPY

(75) Inventors: Zvi Kam, Tel Aviv (IL); Benjamin Geiger, Rehovot (IL)

(73) Assignee: Yeda Research and Development Company Ltd., Rehovot (IL)

( * ) Notice: Subject to any disclaimer, the term of this patent is extended or adjusted under 35 U.S.C. 154(b) by 28 days.

(21) Appl. No.: 10/506,860

(22) PCT Filed: Mar. 13, 2003

(86) PCT No.: PCT/IL03/00206

§ 371 (c)(1),
(2), (4) Date: Sep. 2, 2004

(87) PCT Pub. No.: WO03/077008

PCT Pub. Date: Sep. 18, 2003

(65) Prior Publication Data

US 2005/0121596 A1    Jun. 9, 2005

(30) Foreign Application Priority Data

Mar. 13, 2002  (IL) .................................. 148664

(51) Int. Cl.
*G02B 7/04* (2006.01)
*G02B 27/40* (2006.01)

(52) U.S. Cl. .............................. 250/201.4; 250/484.2; 359/383; 359/368

(58) Field of Classification Search .. 250/201.2–201.4, 250/494.1, 484.2, 461.2, 339.12; 359/383, 359/392, 368
See application file for complete search history.

(56) References Cited

U.S. PATENT DOCUMENTS 4,342,905 A    8/1982  Fujii et al.

(Continued)

FOREIGN PATENT DOCUMENTS

JP    61011714    1/1986

(Continued)

OTHER PUBLICATIONS

Born, M. et al. "Principles of Optics, Electromagnetic Theory of Propagation Interference and Diffraction of Light", Pergamon Press, pp. 369-385 and pp. 413-443, 1959.

(Continued)

*Primary Examiner*—Georgia Epps
*Assistant Examiner*—Suezu Ellis
(74) *Attorney, Agent, or Firm*—Nath & Associates PLLC; Gregory B. Kang; Derek Richmond

(57) ABSTRACT

An auto-focusing method and device are presented for determining an in-focus position of a sample supported on a substrate plate made of a material transparent with respect to incident electromagnetic radiation. The method utilizes an optical system capable of directing incident electromagnetic radiation towards the sample and collecting reflections of the incident electromagnetic radiation that are to be detected. A focal plane of an objective lens arrangement is located at a predetermined distance from a surface of the substrate, which is opposite to the sample-supporting surface of the substrate. A continuous displacement of the focal plane relative to the substrate along the optical axis of the objective lens arrangement is provided, while concurrently directing the incident radiation towards the sample through the objective lens arrangement to thereby focus the incident radiation to a location at the focal plane of the objective lens arrangement. Reflected components of the electromagnetic radiation to a location objective lens arrangement are continuously detected. The detected reflected components are characterized by a first intensity peak corresponding to an in-focus position of said opposite surface of the substrate, and a second intensity peak spaced in time from the first intensity peak and corresponding to an in-focus position of said sample-supporting surface of the substrate. This technique enables imaging of the sample when in the in-focus position of the sample-supporting surface of the substrate.

28 Claims, 11 Drawing Sheets

U.S. PATENT DOCUMENTS

| | | | |
|---|---|---|---|
| 4,595,829 | A | 6/1986 | Neiimann et al. |
| 4,798,948 | A | 1/1989 | Neumann et al. |
| 4,844,617 | A | 7/1989 | Kelderman et al. |
| 5,288,987 | A | 2/1994 | Vry et al. |
| 5,672,861 | A | 9/1997 | Fairley et al. |
| 5,783,814 | A | 7/1998 | Fairley et al. |
| 5,790,710 | A | 8/1998 | Price et al. |
| 5,925,874 | A | 7/1999 | Liegel et al. |
| 5,995,143 | A | 11/1999 | Price et al. |
| 6,128,129 | A | 10/2000 | Yoneyama |
| 6,172,349 | B1 | 1/2001 | Katz et al. |
| 6,259,080 | B1 | 7/2001 | Li et al. |
| 6,441,894 | B1 * | 8/2002 | Manian et al. .............. 356/123 |
| 2001/0033414 | A1 | 10/2001 | Yahiro |

FOREIGN PATENT DOCUMENTS

| | | |
|---|---|---|
| JP | 02190808 | 7/1990 |
| WO | WO 01/90796 A2 | 11/2001 |

OTHER PUBLICATIONS

Wilson, T. et al. "Theory and Practice of Scanning Optical Microscopy", Academic Press, pp. 38-77, 1984.

Geusebroek, J.M. et al. "Robust Autofocusing in Microscopy", *Cytometry*, vol. 39, pp. 1-9, 2000.

Häusler, G. et al. "Imaging with Expanded Depth of Focus", Zeiss Information, vol. 29(98) pp. 9-13, 1987.

Schormann, T. et al. "Contrast enhancement arid depth perception in three-dimensional representations of differential interference contrast and confocal scanning laser microscope images", *Journal of Microscopy*, vol. 166 pt.2 pp. 155-168, 1992.

Stokseth, P.A. "Properties of a Defocused Optical System", *Journal of the Optical Society of America*, vol. 59(10) pp. 1314-1321, 1969.

Hiraoka, Y. et al. "Focal points for chromosome condensation and decondensation revealed by three-dimensional *in vivo* time-lapse microscopy", Nature, vol. 342(6247) pp. 293-296, 1989.

Cheng, Y. et al. "Three-dimensional reconstruction of the actin cytoskeleton from stereo images", *Journal of Biomechanics*, vol. 33 pp. 105-113, 2000.

Agard, D.A. et al. "Three-dimensional architecture of a polytene nucleus", *Nature*, vol. 302 pp. 676-681, 1983.

Agard, D.A. "Optical Sectioning Microscopy: Cellular Architecture in Three Dimensions", *Ann. Rev. Biophys. Bioeng.*, vol. 13 pp. 191-219, 1984.

Swedlow, J.R. et al. "Deconvolution of Images and Spectra", Academic Press, Chapter 9 pp. 286-309, 1997.

* cited by examiner

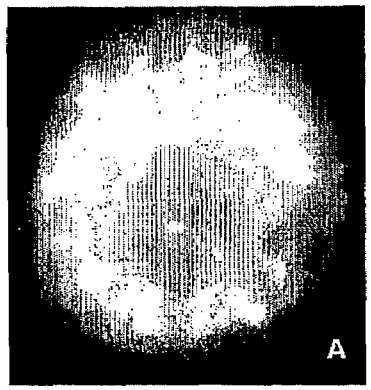 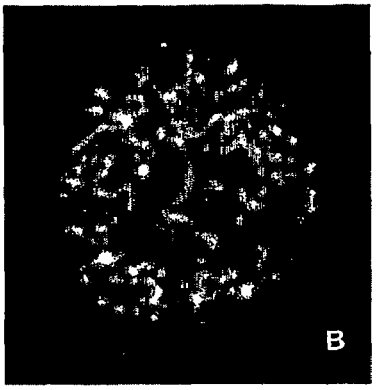 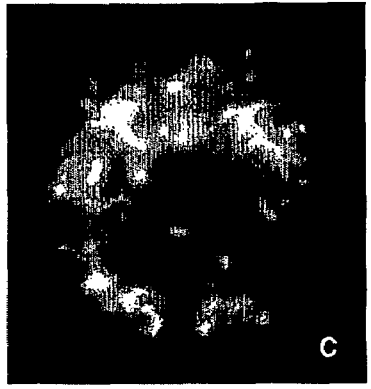
FIG. 11A  FIG. 11B  FIG. 11C
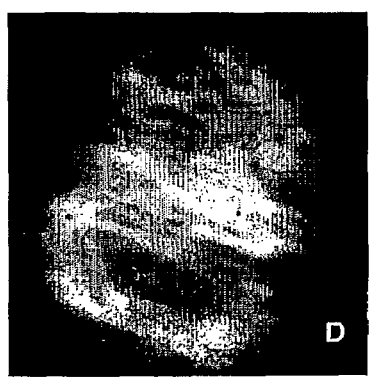 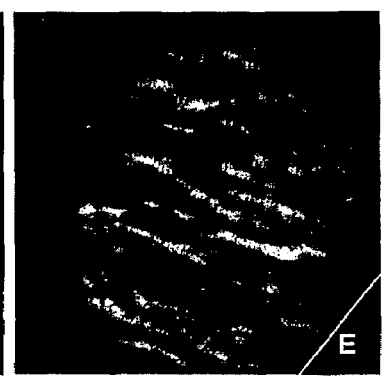 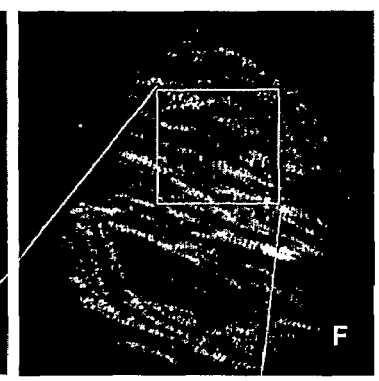
FIG. 11D  FIG. 11E  FIG. 11F
F(enlarged)  FIG. 11G

AUTO-FOCUSING METHOD AND DEVICE FOR USE WITH OPTICAL MICROSCOPY

FIELD OF THE INVENTION

This invention is generally in the field of optical measurement/inspection techniques and relates to an auto-focus method and device, and an imaging system utilizing the same for use with optical microscopy. The invention is particularly useful for the microscope inspection of fluorescently labeled biological specimens on transparent slides.

BACKGROUND OF THE INVENTION

Auto focusing is an essential feature in many automated inspection fields such as the chip industry, biomedical research, data reading/recording in optical information carriers, etc.

Auto-focusing techniques used in the inspection/measurement of such structures as semiconductor wafers typically utilize an optical system separated from an imaging optics, which projects a light pattern (e.g., spots, lines, etc.) on the wafer and optimizes the image of this pattern (by using intensity contrast or displacement). Such techniques are applicable only for long working distance microscopes, i.e., with small numerical apertures. These techniques require calibrations and adjustments to match auto-focusing and imaging optical systems, and are hard to implement, especially when the imaging optics has variable magnification. U.S. Pat. No. 5,925,874 describes a solution to the variable magnification problem based on projecting a focusing pattern through a magnifying imaging optics.

Other common methods for auto-focusing in the chip industry inspection are based on the detection of light reflected from a specimen, wherein incident light is focused either on the outer surface of the specimen, or on inner interfaces of the specimen (as in the case of infrared light).

A recently developed auto-focusing technique for use with measurement/inspection on semiconductor wafers is disclosed in U.S. Pat. No. 6,172,349. This technique is useful in both conventional microscopy and interferometry. According to this technique, an operator designates the area within each field of view where the measurement has to be taken, and, for each area of interest (where the microscope is to be focused), translates the microscope along its optical axis (Z-axis) while measuring the image intensities at discrete sub-areas within the area of interest. These image intensities are then evaluated, and those having the greatest signal-to-noise ratio and occurring at a common point along the Z-axis are selected, and the corresponding sub-areas are identified. During subsequent inspections of the area of interest, only light reflected from the identified sub-areas is used to focus the microscope.

Numerous publications (e.g., Born M. and Wolf, E. Principles of optics Cambridge University Press, 1997; T. Wilson and C. Sheppard, "Theory and practice of scanning optical microscopy", Academic Press, 1984) disclose optical principles, based on detecting the intensity variation above and below a focal plane (z-profile) for a point-like source, which are the basis for many auto-focusing systems.

U.S. Pat. No. 4,595,829 discloses a technique for use with reflected light microscopes. This technique utilizes the production of a measuring point on the surface of an object by an eccentric measuring beam formed by blocking a portion of the path of a full beam, and imaging the measuring point onto a photoelectric device by reflecting the measuring beam along the blocked-out path.

U.S. Pat. No. 4,844,617 discloses an auto-focusing technique for use in the inspection of semiconductor wafers. Here, a confocal microscope utilizes auto-focusing based on maximal intensity evaluated through an aperture larger than the diffraction limited size.

U.S. Pat. No. 5,288,987 describes a focusing technique for stereo microscopy, utilizing the imaging of an incident beam through a cylindrical lens projecting a thin bar-shaped marking on a viewed object surface. In this technique, imaging and focusing are not carried out via the same optics. confocal microscope on the most reflecting layer by an iterative z-scanning of the intensity profile.

U.S. Pat. No. 6,128,129 discloses an auto-focusing technique for a microscope based on the optical path difference to a front focused position and to a back position that are conjugate with respect to the image forming point of the image forming optical system.

U.S. Pat. No. 4,798,948 describes an auto-focusing arrangement for use with incident light microscopes of dark field illumination. According to this technique, an incident light beam is comprised of several (at least two) partial beams which coincide in at least a central region of the incident light beam and which are of different wavelengths. An auto-focus measurement beam is presented by one of these partial beams. A lens element is inserted into the central region of the incident beam so as to change the beam cross-section (converging and diverging).

Some auto-focusing techniques (e.g., U.S. Pat. Nos. 5,995,143 and 5,790,710; and Geusebroek et al., Cytometry, 39:1–9 (2000) and references cited therein) are based on the analysis of image contrast and local intensity distributions. These techniques typically require the acquisition and analysis of many images to reach the best focus. The application of these techniques for fluorescence microscopy of biological samples is described in U.S. Pat. No. 6,259,080, where the maximal signal to background value criterion is used. Here, a shutter is added to block the excitation illumination between image acquisition periods, thus minimizing the sample bleaching. The focusing technique of U.S. Pat. No. 5,790,710 is intended for use in a scanning microscope for inspecting fluorescently stained biological samples. This technique is aimed at avoiding bleach and phototoxicity utilizing the phase-contrast microscope image.

Auto-focusing techniques utilizing an increase of the depth of focus of a focusing optics by digital combination of series of images taken at many close focal planes are disclosed, for example, in the following publications: Haeusler, G. and Koemer, E., "Imaging with Expanded Depth of Focus", Zeiss Inform., Oberkochen, 29:9–13, No.98E., (1986/87); Schormann, T. and Jovin, T. M., "Contrast Enhancement and depth perception in three-dimensional representation if differential interference contrast and confocal scanning laser microscope images.", J. Microscopy 166:155–168, (1992). According to these techniques, a plurality of images is taken and processed three-dimensionally to find the sharpest features of all focal planes which are presented in the single "deep focus" image. Additionally, these techniques are not preserving intensities, and therefore are not applicable for quantitative fluorescence microscopy applications.

Present automated high-resolution (high-content) high-throughput applications of light microscopy in biology require scanning a large number of samples, such as cell yeast or bacteria, typically inside multi-well micro-plates, and acquiring images in each well which resolve intracellular details at the utmost resolution possible by the optics. In order to resolve such details, setting the focus within the vertical focal resolution of the objective is mandatory. This means 0.3–0.5 µm for immersed objectives, and 0.6–0.9 µm for high-numerical aperture long-working-distance air objectives. Such accuracy is far beyond the tolerance of the bottom surfaces of multi-well dishes, and even typical high-performance XYZ stages cannot scan distances of about 10 cm in the XY plane while keeping the Z coordinate within the above tolerances.

A practical solution for the existing instruments is to find the focus for a given sample, based on the optimization of image sharpness. Different algorithms, employing Fourier frequency space and real space image analysis, have been used, and Z scan, in a range that is expected to include the optimal focus, can guarantee that the best focal plane will be found (Geusebrock et al., Cytometry 39:1–9 (2000) and references 1–8,10–11,25–26 cited therein). To accelerate the process, the scan is first made in large steps, and refined till the required focus accuracy is reached. However, this approach has several inherent problems:

1. The process is slow. Even if processing is performed in real time, at least an order of magnitude slower throughput is expected as compared to maximum possible image acquisition rate.

2. A focus search algorithm could be based on efficient optimization. For example, Fibonacci minimization can reduce the range of the minimum search from 0.3 mm to 0.3 µm in 12 steps. Yet, there is no scheme that will map the distance from the focus into any evaluation parameter with smooth dependence displaying a single minimum over three orders of magnitude range of defocusing. Scans must therefore start close to the focus (typically within 20 µm) to refine its position 3. Sharpness criteria are very sensitive to dirt, scratches and fingerprints on surfaces. Glass slides or plastic well bottoms are a fraction of a millimeter thick and may often cause auto-focus devices based on maximal sharpness to focus at the wrong side of the sample substrate.

4. Sharpness algorithms are context-dependent, and there is no global focus criterion that can equally apply to a wide variety of image types. Fluorescently tagged cells may be found by the virtue of the cell-specific staining. However, image-based focusing is not applicable to fluorescent microscopy, where repeated imaging may cause bleach and phototoxicity. Fluorescence is localized also to specialized sub-volumes, thus the intensity varies greatly and is sample dependent. Typical biological screens based on fluorescent labels need to report intensities over a widely distributed range, as well as their absence. Focusing methods that evaluate fluorescence are therefore not applicable for such screens.

5. Biological specimens (such as live cells) are basically transparent, and have very low reflectivity, usually from structures (such as organelles) dispersed through their whole volume. Transmitted light microscopy can acquire images by optical contrasting methods (such as DIC or phase contrast) that avoid photo-toxic fluorescence excitation. Yet, even if the focus reaches a plane somewhere within the extent of the cell height, typically 4–10 µm, some subcellular details may still be out-of-focus. To assure the covering of the whole cell height by three-dimensional (3D) optical sectioning methods, one needs to over-scan a focal range about twice as high as the cell, since the initial plane may be close to the bottom or the top of the cell. Phase images may have the best contrast at focal heights that depend on irregular structures within or above the sample, and hence, cellular details may still be blurred for high resolution imaging. Phase images may also produce the best contrast at under- or over-focus conditions due to the nature of phase-optics and due to the misalignment of the phase ring optics.

SUMMARY OF THE INVENTION

There is accordingly a need in the art to facilitate the auto-focusing and inspection of samples, particularly biological samples, by providing a novel auto-focusing method and device, and an imaging system utilizing the same.

The technique of the present invention provides for inspecting a sample supported on a plate-like substrate transparent with respect to incident radiation. The main idea of the present invention consists of detecting an in-focus position of the substrate's surface supporting the sample by continuously varying the relative distance between the sample and an objective (generally, focusing optics) along the optical axis of the objective so as to scan the substrate's thickness (height), while continuously directing incident radiation towards the substrate through the objective and detecting reflections of the incident radiation collected by said objective. This technique enables the sequential detection of two reflected intensity peaks, wherein the first detected peak corresponds to the in-focus position of the surface of the substrate closer to the objective, and the second detected peak corresponds to the in-focus position of the other opposite surface of the substrate, which carries the sample. This technique thus provides for a very fast in-focus positioning of the sample-carrying surface.

There is thus provided according to one aspect of the present invention, an auto-focusing method for determining an in-focus position of a sample supported on one surface of a substrate plate made of a material transparent with respect to incident electromagnetic radiation, the method utilizing an optical system capable of directing incident electromagnetic radiation towards the sample and collecting reflections of the incident electromagnetic radiation which are to be detected, and comprising:

(a) locating a focal plane of an objective lens arrangement at a predetermined distance from the other surface of the substrate, which is opposite to said surface supporting the sample;

(b) providing continuous displacement of the focal plane relative to the substrate along the optical axis of the objective lens arrangement, while concurrently directing the incident radiation towards the sample through the objective lens arrangement to thereby focus the incident radiation to a location at the focal plane of the objective lens arrangement; and (c) continuously detecting reflected components of the electromagnetic radiation collected through said objective lens arrangement, said detected reflected components being characterized by a first intensity peak corresponding to an in-focus position of said opposite surface of the substrate, and a second intensity peak spaced in time from the first intensity peak and corresponding to an in-focus position of said sample-supporting surface of the substrate, thereby enabling imaging of the sample when in the in-focus position of the sample-supporting surface of the substrate.

Thus, when reaching the in-focus position of the sample-supporting surface of the substrate, one or more images of the sample can be acquired with the substrate being stationary located with respect to the objective lens arrangement. This technique is suitable for the case when cell-substrate contacts are of interest, and they appear in focus at the level of the substrate interface.

A series of images ("focal series" presentation of the 3D sample) can be acquired for different positions of the focal plane of the objective starting at the sample-supporting surface of the substrate using the in-focus position of the sample-supporting surface as a reference height.

Alternatively, upon reaching the in-focus position of the sample-supporting surface of the substrate, an indication signal can be generated to actuate an imaging channel for a certain time period, while continuing the relative displacement between the focal plane of the objective lens arrangement and the substrate, through the sample. A series of pixel array images of successive planes of the sample along the optical axis of the objective lens arrangement is thus integrated on the imaging detector. This is the so-called "sweeping focus imaging mode", which results in data representation of the 2D projection of the 3D sample onto a two-dimensional pixel array of the detector.

Preferably, the displacement of the focal plane relative to the substrate is carried out with a higher speed until the first intensity peak is detected, and is then slowed until the second intensity peak is detected. Thus, a very fast approach to focus can be achieved from afar, but no mechanical overshoot will be experienced when reaching the in-focus position of the substrate's surface.

When dealing with biological samples having fluorescent labels, the incident radiation used for auto-focusing is of a suitable wavelength range incapable of causing luminescent response of the sample.

The sweeping focus technique of the present invention further provides for obtaining the real 2D-projection image of a 3D sample. This is implemented by two-dimensional deconvolution with the predetermined Point Spread Function of a sweeping-focus mode, thereby resulting in an image of the 2D projection of the 3D sample.

Thus, according to another aspect of the present invention, there is provided a method for obtaining an image of a three-dimensional sample in the form of a two-dimensional projection of the sample, which is supported on a substrate plate made of a material transparent for incident radiation, the method comprising the steps of:

(a) providing data representative of images of successive planes of the sample along the optical axis of an objective lens arrangement continuously acquired by a two-dimensional pixel array of a detector during a continuous relative displacement between the focal plane of the objective lens arrangement and the substrate through the sample;

(b) processing said data by carrying out a two-dimensional deconvolution thereof with the predetermined Point Spread Function of an imaging system, thereby obtaining said image in the form of the two-dimensional projection of the three-dimensional sample.

According to yet another aspect of the present invention, there is provided an auto-focusing device for determining an in-focus position of a sample supported on the surface of a substrate plate made of a material transparent with respect to incident electromagnetic radiation, the device comprising:

a light source generating a beam of the incident radiation of a predetermined wavelength range;

a focusing optics including an objective lens arrangement;

a light directing assembly, which is operable for directing the incident beam towards the sample through the objective lens arrangement with a predetermined numerical aperture of beam propagation to irradiate a diffraction-limited point on the focal plane of the objective lens arrangement, and for directing reflections of said incident radiation collected by said objective lens arrangement to a detector unit which is operable to detect said reflections and generate data indicative of their intensities;

a drive assembly operable to provide continuous displacement between the focal plane of said objective lens arrangement relative to the substrate along an optical axis of the objective lens arrangement; and a control unit for operating said drive assembly to provide said continuous relative displacement and instantaneous stop of the displacement, for operating said light source and said detector to allow continuous detection of said reflections during said relative displacement, said control unit comprising a processing device operable to be responsive to said data generated by the detector unit to identify a first intensity peak corresponding to the in-focus position of a surface of said substrate opposite to the sample-supporting surface of the substrate, and identify a second intensity peak spaced in time from the first intensity peak corresponding to the in-focus position of the sample-supporting surface of the substrate, and to generate an auto-focusing signal upon detecting said second intensity peak.

According to yet another aspect of the invention, there is provided an imaging system comprising said auto-focusing device and an imaging device, which comprises a light source and a detector.

The present invention provides for a very fast auto-focusing technique. The focus swept time until the in-focus position of the sample-supporting surface is reached, depends practically on the time needed for mechanical focus adjustment, since the whole process is performed by closed-loop hardware control, e.g., a piezo-mounted objective having a millisecond response. The in-focus signal (intensity peak) is strong, falling sharply with the movement of the respective surface away from the in-focus position, and has a well defined magnitude which is independent on the sample and therefore can easily be identified by a very fast focal sweep, without being disturbed by weak signals associated with the sample. The magnitude of the signal is known (from a suitable calibration procedure) and provides for identifying the in-focus position of the two opposite surfaces of the substrate.

By using red (or infrared) light in the focusing apparatus, bleaching or photo-damage of the sample is avoided. The technique is therefore ideally suitable for inspecting live samples, such as GFP tagged cells. The method of the present invention is also suitable for thick samples, where no focal height of any absolute sense can be defined. The auto-focusing method of the invention sets on the substrate-slide surface forming the lower limit (closest to the objective) Z-focus of the 3D sample. The system offers a very high speed factor in the imaging and analysis of three-dimensional samples, since the exact edge of the cell volume (sample-supporting surface of the substrate) is determined avoiding the need for over-scanning focal planes.

Preferably, the auto-focusing incident beam is expanded to fill the back aperture defined by the objective lens arrangement. The light directing assembly of the auto-focusing device comprises a beam splitting device for separating the paths of the incident and reflected light components propagating towards and away from the objective, respectively, through the auto-focusing channel.

The imaging system preferably comprises a notch-or a high-pass wavelength-selective reflector, which separates the wavelength components propagating through the auto-focusing and imaging channels, in such a manner that the auto-focusing channel does not block a part of the imaging aperture. By using the identical optics (objective) for imaging and focusing and by filing the back aperture defined by the objective lens arrangement, the focus accuracy is automatically matched to the diffraction-limited values characterizing the optimal imaging of the sample.

The method of the present invention is applicable for transparent samples, such as biological cells. No reflection, scattering or fluorescence from the sample itself is used. The method is independent on the microscope imaging mode or sample type, and is effective even when some fields in the specimen do not have cells or have cells that are not labeled. Being an imaging-independent method, the present invention can be used with various imaging modes (phase, Nomarskii Differential Interference Contrast (DIC) or fluorescence). The present invention can utilize air objectives, as well as the highest NA immersion objectives. The present invention as described below uses confocality principles, but it should be understood that it is operable with wide-field microscopes as well, without affecting the imaging optical path.

For the inspection of a fluorescently labeled biological sample, an accessory red or infrared laser beam is employed to adjust the objective focus and find the substrate on which biological tissue cells are grown. The laser light can be switched on for focusing and switched off during imaging, or it may be left on permanently, and filtered out from the imaging optical path by the combination of the emission filter and the reflection in a specially designed wavelength-selective reflector which acts as a notch reflector for the laser wavelength, and is transparent to other colors.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 11A to 11G illustrate examples of a cell stained for its mitochondria and a muscle cell stained for myosin, showing, for each cell respectively, a sweeping-focus 2D-deconvolved image of the samples, and a 3D-deconvolved and projected image of the same samples;

DETAILED DESCRIPTION OF THE INVENTION

Figure 1:
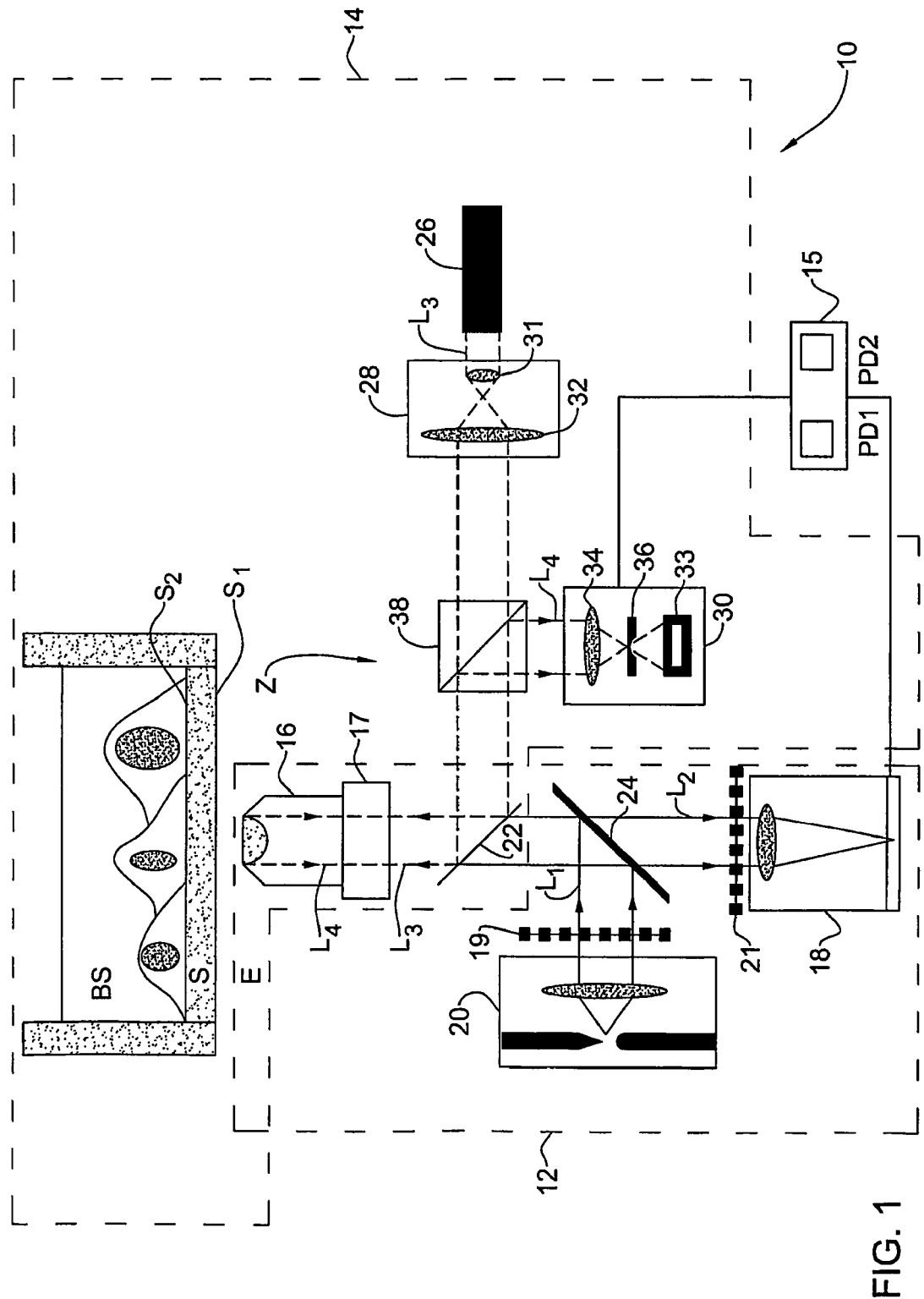
FIG. 1 schematically illustrates an imaging system for inspecting a biological sample that utilizes an auto-focusing device according to the invention.

Referring to FIG. 1, there is illustrated an imaging system 10 for acquiring images of a sample, a biological sample BS in the present example. The system comprises such main constructional parts as an imaging device 12 and an auto-focusing device 14 associated with a control unit 15 connectable to the elements of the auto-focusing and imaging devices, as will be described more specifically further below. As shown, the biological sample BS (typically a sample chamber including a buffer layer in which cells are grown) is located on the surface $S_2$ of a substrate S (glass/plastic slide). The system 10 is located at the opposite surface $S_1$ of the substrate. The substrate is supported on a stage (not shown) movable in a plane perpendicular to the Z-axis.

The control unit 15 comprises a processing utility $PD_1$ operable to process data coming from the auto-focusing device 14 to generate a focusing signal indicative of the in-focus position of the sample-carrying surface for actuating the imaging device 12. The latter can thus acquire images of the sample BS, when in the in-focus position thereof. The technique of the present invention also provides for obtaining an image of the two-dimensional projection of a three-dimensional sample. To this end, the control unit 15 comprises a further processing utility $PD_2$ preprogrammed to carry out a two-dimensional deconvolution of detected data, as will be described further below. It should be understood that the processing utility $PD_2$ may be incorporated in a separate unit connectable to the output of an imaging detector.

The imaging and auto-focusing devices 12 and 14 utilize a common objective lens arrangement 16 (which in the present example is composed of a single lens, but can generally be composed of more than one lens), and define imaging and auto-focusing channels of light propagation. To facilitate illustration, the light propagation through the imaging and auto-focusing channels is shown schematically: light component denoted $L_1$ and $L_2$ propagate through the imaging channel, and light component $L_3$ and $L_4$ propagate through the auto-focusing channel. As further shown in the figure, a shutter 19 is located in front of the light source 20, and is selectively operated to allow irradiation of the sample with the incident light $L_1$ to enable imaging of the sample.

The system 10 also comprises a suitable drive assembly operable by the control unit 15 to provide relative displacement between the objective 16 (i.e., its focal plane) and the sample BS along the optical axis of the objective (Z-axis) during the auto-focusing procedure (Z-scan). Generally, such a drive assembly can be associated with either one of the objective lens 16 and the sample BS. In the present example, the objective lens 16 is driven by a servomotor (e.g. piezo-drive) 17, operable by the control unit 15, for moving the objective along the Z-axis relative to the sample.

Considering the specific example of the invention where the system 10 is intended for inspecting the biological sample BS of the kind having fluorescent labeling, the imaging device 12 utilizes an appropriate light source 20 (such as Mercury or Xenon arcs or Metal Halide lamps) for generating the incident light $L_1$ of a wavelength range capable of exciting the sample to cause a fluorescent response thereof $L_2$. The light response $L_2$ is collected by the objective 16 and directed to an imaging detection unit 18 (e.g., comprising an area CCD associated with suitable imaging optics and imaging shutter 21). A light directing assembly of the system 10 includes a wavelength-selective beam-splitting device 24 designed to reflect the wavelength range of the incident exciting light $L_1$ and transmit the wavelength range of the fluorescent excited light $L_2$ thereby preventing wavelength components of the incident exciting light $L_1$ from reaching the imaging detector 18 and allowing detection of the fluorescent light $L_2$.

The substrate S is transparent with respect to incident radiation of both autofocusing and imaging wavelengths, as well as for the fluorescent excited light. The surface $S_1$ presents an interface between the glass/plastic substrate S and the environment E (e.g., air or immersion liquids).

To spatially separate between light components propagating through the imaging and autofocusing channels, the light directing assembly of the system 10 further employs a wavelength-selective beam splitting device 22 (e.g., dichroic mirror, for example the Cat# 633DCRB STOCK #23416 model commercially available from Chroma, VM). The beam splitting device 22 is constructed so as to transmit a wavelength range including the wavelength of the incident exciting light $L_1$ and that of the fluorescent response $L_2$, and to reflect any other wavelength range of light propagating through the auto-focusing channel (light components $L_3$ and $L_4$).

The auto-focusing device 14 comprises a light source (laser) 26 operating in an appropriate wavelength range— the red or infrared wavelength range in the present example (e.g., Uniphase 2 mW He—Ne); a beam expander assembly 28; the beam directing assembly including a beam splitting device 38; the objective lens arrangement 16; and a detection unit 30. The use of red (or infrared) light for autofocusing purposes avoids sample bleaching or photo-damage, and is therefore ideally suited for live samples, such as GFP tagged cells.

The detection unit 30 comprises a detector 33 of the kind generating an electrical response to light signal impinging thereon (e.g., a PIN diode detector, for example the UDT PIN 10DF model commercially available from United Detector Technology), which is associated with a suitable imaging optics, composed of an imaging lens 34 and a confocal pinhole 36 in the present example. The provision of the pinhole 36 is aimed at rejecting (filtering out) more efficiently light components reflected from out-of-focus locations, and sharpening the detected intensity peak corresponding to the light components reflected from the in-focus locations.

The beam splitting device 38 (typically a partially transparent mirror or 50% reflecting cube) is used for spatially separating between the light beam $L_3$ emitted by the laser 26 and reflections thereof $L_4$ to thereby enable propagation of the reflections $L_4$ only to the detector 33. It should be noted that the use of the partially transparent mirror or 50% reflecting cube as the beam splitter 38 in the auto-focusing channel results in that 75% of the incident and reflected power is lost because of passing twice through the semi-transparent surface of the beam splitter 38. These losses can be reduced by using polarized light and a polarization controlling assembly (polarizing beam splitter). More specifically, this can be implemented by using a linearly polarized light $L_3$ passing through a polarizing surface of the beam splitter 38, and a polarization rotating element (e.g., $\lambda/2$ wave-plate) in the optical path of light $L_4$ returned from the sample to adjust the polarization of light $L_4$ to be reflected from the polarizing surface of the beam splitter 38 towards the detector unit 30. The linearly polarized light $L_3$ can be achieved by using the highly polarized light source 26, or by using a polarizer in the optical path of randomly polarized light generated by the light source 26. Preferably, in order to use all the light generated by the light source, such a polarizer includes a polarization splitting means, a polarization rotator in a path of one polarization component, and a polarization combining means. The polarization splitting and combining means may be constituted by the same polarizing beam splitter/combiner, provided an appropriate set of light reflectors is used.

The expander assembly 28, which in the present example is composed of two lenses 31 and 32, provides for expanding the width of a beam $L_3$ emitted by the laser 26 to thereby fill the back aperture defined by the objective lens arrangement 16. By changing slightly the distance between the two lenses in the assembly 28, it is possible to set the converging point of the laser beam $L_3$ in front of or behind the imaging focus. The focal lengths of the two lenses 31 and 32 determine their effect on the beam's cross-section width, and provide for matching the width of the beam so as to fill the entire back-aperture, and to enable the objective to focus the focus-sensing beam to a diffraction-limited size defined approximately by the equation:

$$Res = \lambda/2NA$$

wherein $\lambda$ is the wavelength of the laser beam impinging onto the beam expander assembly, and $NA = n(\sin \theta)$ is the numerical aperture of the objective, n being the index of refraction of the environment E in front of the objective (e.g., air, or immersion liquids) and $\theta$ being half the solid angle of the light beam after being focused by the objective.

Thus, the emitted beam of light $L_3$ is expanded by the assembly 28 to be thereby capable of filling the back aperture defined by the objective lens 16. The expanded light beam $L_3$ propagates through the beam splitter 38 and is then reflected by the wavelength-selective surface of the device 22 towards the objective lens 16, which focuses the beam onto a diffraction-limited location on the focal plane of the lens 16.

The auto-focusing procedure is aimed at locating the sample-supporting surface $S_2$ of the substrate in the focal plane of the objective lens 16. This is implemented by adjusting the focus of the objective to the first interface $S_1$ and thereby yielding a first approximation to the position of the second interface $S_2$ at the other side of the substrate slide where cells grow.

It should be understood that the imaging focus defined by the objective lens 16 (i.e., the laser auto-focusing point of convergence) and the confocal pinhole 36 in front of the auto-focusing detector are located in conjugated planes. By using the identical optics for imaging and focusing and by filing the entire numerical aperture of the imaging objective, the focus accuracy (z-resolution) is automatically matched to the diffraction-limited values characterizing the optimal imaging of the specimen. On the other hand, the autofocusing wavelength is split away from the imaging channel, and the detector 33 and pinhole 36 do not block any part of the imaging aperture.

During the Z-scan (varying the distance between the objective and the substrate along the optical axis of the objective), the incident auto-focusing beam $L_3$ is sequentially reflected by substrate's surfaces $S_1$ and $S_2$, and these sequential reflections $L_4$ propagate through the auto-focusing channel towards the detection unit 30 (i.e., pass through the objective lens 16 and are then reflected from the wavelength-selective surface of the device 22). The surface $S_1$ presents either one of air-glass, air-plastic and immersion liquid-glass interfaces, whatever the case may be, and the surface $S_2$ presents a glass-buffer or plastic-buffer interface. The fraction of light reflected at an interface is proportional to the difference in refractive indices of the two media at opposite sides of the interface, which is about 4% for air-glass interface (i.e., surface $S_1$ which is located closer to the objective), and is about 0.8% for the glass-buffer interface (i.e., surface $S_2$ on which cells are grown). For a 2 mW HeNe laser used as the light source 26 in the auto-focusing device 14, the auto-focusing detector 33 behind the pinhole 36 should theoretically accept 20 μW (calculated as the product of (2 mW)×(4% reflection)×¼) from the air-glass substrate reflection, and 4 μW from the glass-buffer interface reflection. Experiments have shown that, with the 2 mW energy of the emitted light beam $L_3$, 0.7 mW energy is reflected from the substrate's surface $S_2$ and 7 μW energy reaches the detector 33, which is accounted by the objective transmission (80%), slightly overfilling the back aperture, and selective reflector efficiency (80% twice).

Figure 2A:
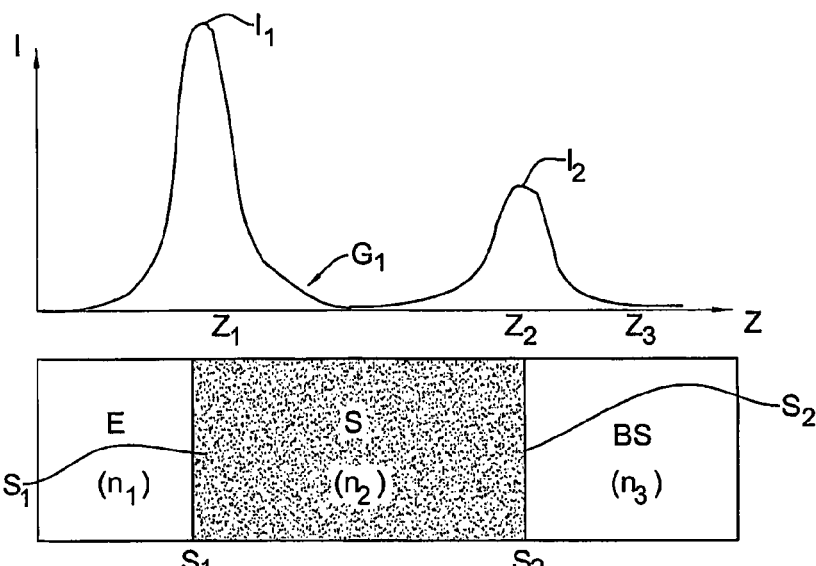
FIGS. 2A to 2C illustrate the principles of the auto-focus detection method according to the invention, for three different examples, respectively, of air and immersion liquids filling the space between the objective and the substrate's surface supporting the sample.
Figure 2B:
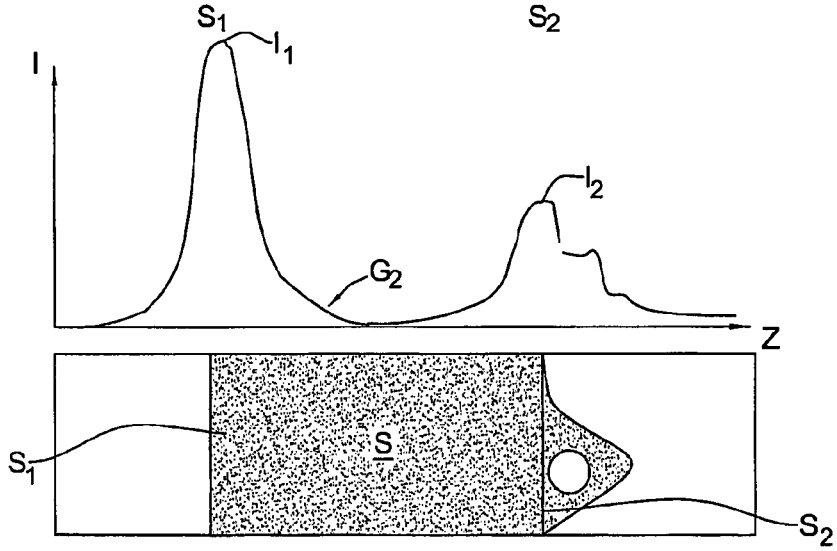
Figure 2C:
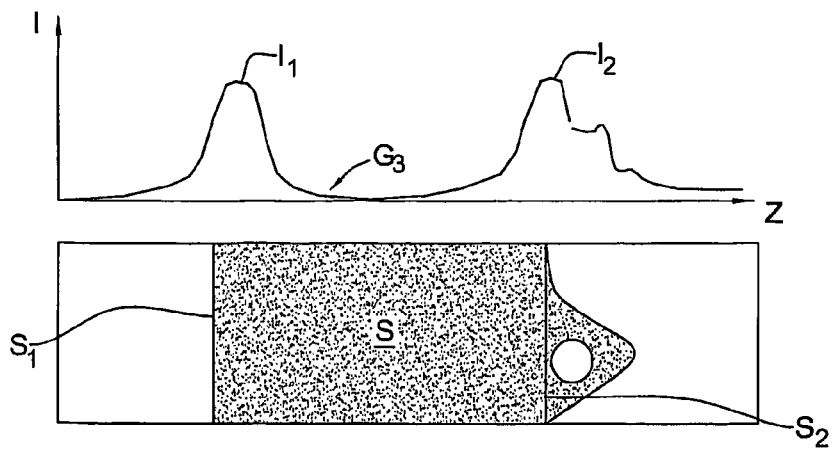

Reference is made to FIGS. 2A–2C showing the principles of the auto-focusing technique of the present invention for three different examples of interfaces defined at the substrate's surfaces $S_1$ and $S_2$. In the example of FIG. 2A, a clean buffer sample BS (water or solution with $n_3$=1.33) is located on the surface $S_2$ of the glass substrate S ($n_2$=1.52), and the environment at the other side of the substrate is air ($n_1$=1). In other words, the surfaces $S_1$ and $S_2$ present, respectively, air/glass and glass/water interfaces. In the example of FIG. 2B, the surfaces $S_1$ and $S_2$ present air/glass and glass/cells-in-buffer ($n_3$ of about 1.33–1.35) interfaces. FIG. 2C presents an example with immersion/glass and glass/cells-in-buffer interfaces.

FIGS. 2A–2C show graphs $G_1$–$G_3$, respectively, representative of data continuously detected by the auto-focusing detector (33 in FIG. 1) during the z-scan. Each of these graphs is in the form of the intensity I(z) of the detected reflected light $L_4$ as a function of the Z-positions of the focal plane of the objective 16 relative to the substrate S. These data are obtained while displacing the focal plane of the objective with respect to the substrate. At this stage, the imaging device is in its inoperative position, i.e., the shutter 19 in front of the imaging light source is closed.

As shown, each function I(z) is characterized by two intensity peaks $I_1$ and $I_2$ with maximal values when the surfaces $S_1$ and $S_2$, respectively, are at $Z_1$ and $Z_2$ positions. These intensity peaks correspond to the in focus positions of the surfaces $S_1$ and $S_2$, since these surfaces are the only two boundaries of change in the index of refraction in the path of laser light $L_3$ towards the specimen. It should be understood that the Z-scanning starts from the focal plane position a certain distance (of about one millimeter) from the substrate, and the peak $I_1$ therefore appears first. The graphs $G_1$–$G_3$ differ from each other in the intensity values of the peaks, due to different interfaces, i.e., different values of $(n_2-n_1)$ and $(n_3-n_2)$.

Figure 3:
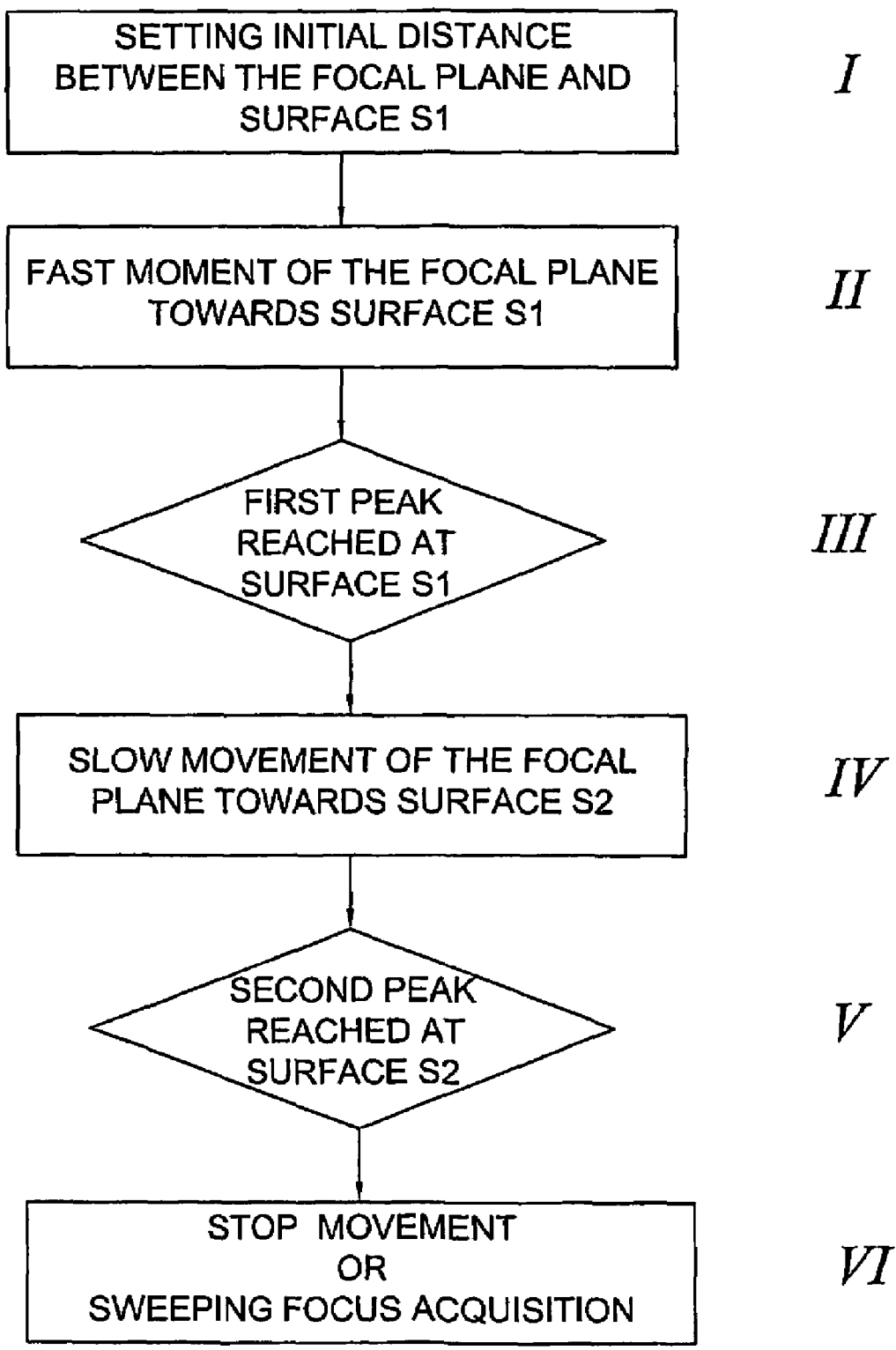
FIG. 3 is a flow diagram of the main operational steps in the auto-focusing method of the present invention.

The main steps in the auto-focusing method of the present invention will now be described with reference to FIG. 3. At the initiation of the auto-focusing session, the focal plane of the objective 16 is spaced from the substrate (its surface $S_1$) a certain distance, e.g., is set to be of about one millimeter (step I). During the repeated automated setting of the focal plane positions along the substrate, this initial distance is set by the mechanical tolerance of the sample and stage height changes, which, for improved design, may be less than 100 μm. The displacement of the focal plane of the objective is then handled by suitable hardware of the control unit 15, associated with the servomotor 17 displacing the objective as shown in the example of FIG. 1 (or associated with the substrate, whatever the case may be), and controlling the illumination and camera exposure shutters 21. This hardware operates to provide a very fast movement of the focal plane of the objective towards the substrate (step II), until the intensity of the detected reflected light $L_4$ reaches its maximal value $I_1$ (the first Z-derivative of the intensity is equal to zero) and the intensity value is higher then a preset threshold defined by the nature of the interface between the substrate and environment (step III). This corresponds to the in-focus position of the substrate's surface $S_1$. Then, the objective slows down (step IV) and sets a trigger (step VI) when the second peak $I_2$ is detected (step V), being defined by a respective threshold value in accordance with the environment. This second intensity peak corresponds to the in-focus position of the substrate's surface $S_2$ supporting the sample. It should be noted that it is possible to move the lens 32 with respect to lens 31 of the expander unit 28 and set the peak slightly before the imaging focus of the objective reaches the surface $S_2$, thus enabling to set the initial focus at any prescribed distance before the actual cells are in focus, for example for over-height sampling purposes to cover out-of-focus contributions. The trigger may stop the focal displacement. The control unit 15 thereby either actuates the imaging device 12 to carry out a computerized 3D acquisition of focal series, or continues the focal plane displacement through the sample, while the excitation and camera exposure shutters are opened to initiate a sweeping-focus image acquisition mode, as will be described below. The use of such an auto-focusing intensity pattern provides for accelerating the auto-focusing procedure, which is important for the high-throughput inspection of biological samples.

Turning back to FIGS. 2A–2C, a broader and noisy tail for the second peak $I_2$ in the example of FIG. 2B associated to the side away from the objective is caused by the provision of a non-homogeneous medium of the buffer containing cells on the surface $S_2$. This does not affect the performance of detecting the peak when approaching from the objective direction. Notwithstanding these differences in the intensity pattern, it is evident that the method of the present invention provides robust focusing results for all three cases.

Figure 4:
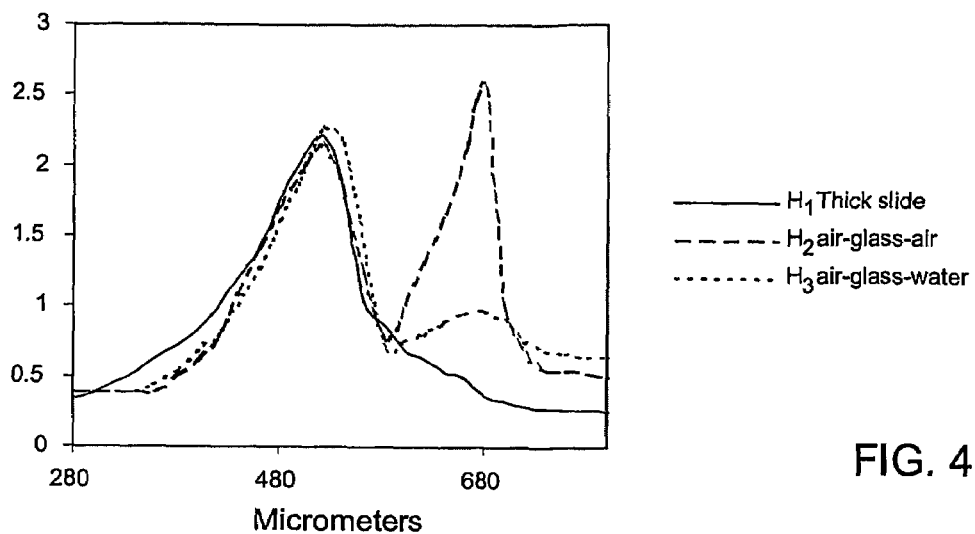
FIG. 4 illustrates experimental results of the intensity profile of light reflected from different substrate-sample interfaces of the examples of FIGS. 2A and 2B.

FIG. 4 illustrates experimental results showing three intensity patterns $H_1$–$H_3$ (i.e., intensity changes during the z-scan) obtained by reflecting light from three glass slides (substrates), respectively, through a 40× microscope objective with a 0.75 numerical aperture and a 5 μm pinhole. Graph $H_1$ corresponds to a 1 mm thick slide. In this example, the first peak only is detected, i.e., the focal plane position at the front surface closer to the objective ($S_1$ in FIG. 1). This is associated with the fact that the sweeping range is smaller than the slide thickness (the focal plane displacement is only over 0.5 mm), the focus thus never reached the sample-carrying surface of the substrate ($S_2$ in FIG. 1). Graph $H_2$ presents the case with a thin cover-slide (of a 180 μm thickness) in air, i.e., air-glass-air interfaces. Here, the first and second intensity peaks are shown (reflections from both surfaces $S_1$ and $S_2$) which are close in amplitude. Graph $H_3$ is the intensity profile obtained with the same thin slide (160 μm thickness) but with a water layer covering its back surface ($S_2$ in FIG. 1), i.e., air-glass-water interfaces. As shown in graph $H_3$, the reflection from the glass-water interface (second peak) is 5 times weaker than that of the air-glass interface (first peak), which is in agreement with theoretical prediction.

As indicated above, as the focus is swept, the auto-focusing detector (33 in FIG. 1) records a sharp peak of intensity with a maximum when the first surface $S_1$ of the substrate (typically glass-air interface) is in focus. The width of the intensity peak, i.e., the fall rate of the intensity from the maximal value, is dependent on the defocus D (a distance between the plane defined by the substrate's surface $S_1$ and the focal plane of the objective, which is also the converging point of the laser light). The steepness of the peak can be regulated by the confocal pinhole aperture (36 in FIG. 1) in front of the detector. The role of the pinhole in the auto-focusing technique will now be more specifically described with reference to FIGS. 5A and 5B.

Figure 5A:
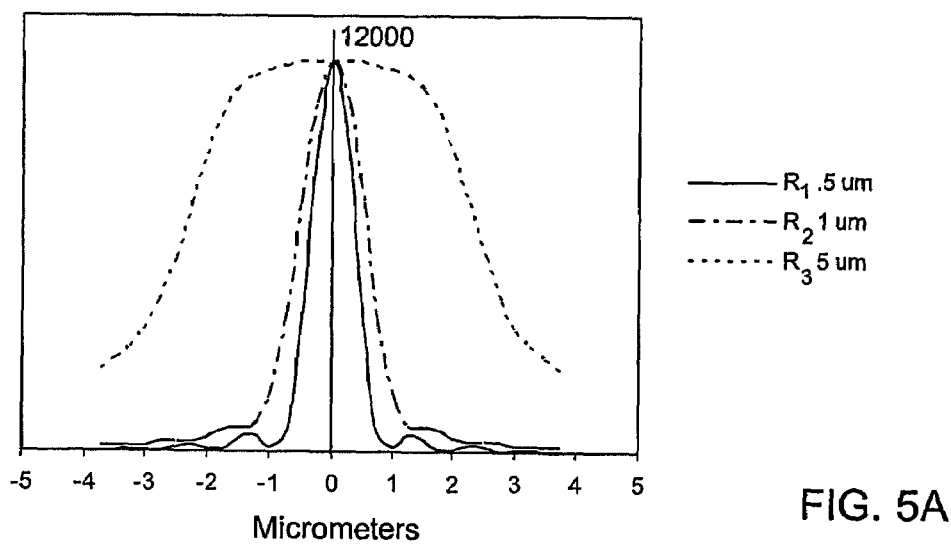
FIGS. 5A and 5B illustrate experimental results showing the role of a pinhole aperture located in the detector path of the auto-focusing device of FIG. 1.

FIG. 5A illustrates the simulation of the intensity of the detected light as a function of defocus D. In this example, the reflections $L_2$ from the laser beam focused spot on the sample-supporting surface of the substrate are calculated. The calculations of the z-focus dependence of the Point Spread Function (PSF) intensity inside the circles were carried out using the Stokseth theoretical model (J. Opt. Soc. Am., 59, p. 1314–1321, 1969). The intensity in the image was integrated in the appropriate pinhole size for the purpose of simulating variable pinhole measurement. This configuration can actually be implemented in a digital microscope with minimal modification to find the substrate surface. To eliminate the detection of the laser reflections $L_4$ of the auto-focusing radiation, in case the emission filters are not sufficiently effective, the auto-focusing channel must be turned off during imaging. In this case, however, the focusing process is longer due to the relatively slow reading rate of images. Three graphs (intensity peaks) $R_1$–$R_3$ are shown corresponding to different diameters of the annular pinhole apertures of, respectively, 0.5 μm, 1.0 μm and 5 μm. It should be understood that these aperture dimensions are considered as the pinhole equivalents in the object plane. It is evident that the steepness of the decaying intensity peak can be broadened by opening the confocal pinhole aperture.

Figure 5B:
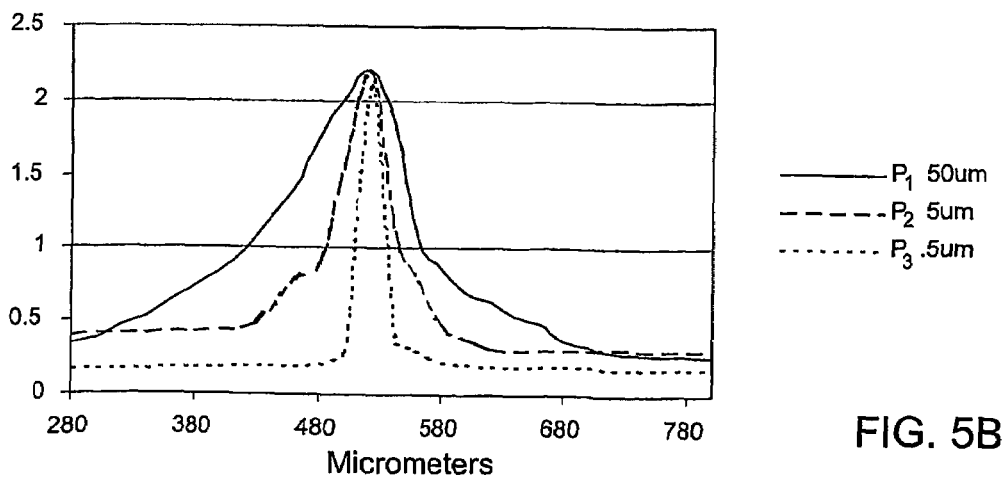

FIG. 5B shows experimental measurements by the auto-focusing detector (33 in FIG. 1). Graphs $P_1$, $P_2$ and $P_3$ correspond to the intensity profile along the Z-axis for the pinhole openings of 50 μm, 5 μm and 0.5 μm, respectively (i.e., pinhole equivalents in the object plane). For pinhole openings much larger than the diffraction-limited focused laser spot size, the detected intensity falls from its peak at the focus within a range comparable to the focal length of the objective. This range can be narrowed by closing the pinhole. Dynamic control of the pinhole opening facilitates the detection of the intensity gradient while approaching (fast) the in-focus location of the substrate plane from far away, and is used to tune the speed of this motion towards the in-focus position in a critically damped close loop. For the precise detection of the in-focus position, the pinhole should be closed to the diffraction size.

As indicated above, when the in-focus position of the sample-supporting surface $S_2$ of the substrate is detected, the control unit 15 actuates the imaging device 12. At this stage, one or more images of the sample at the in-focus position of the surface $S_2$ and other positions at set distances from this surface can be carried out. To this end, the shutter 19 is shifted into its open position, and the light source 20 of the imaging device generates incident light $L_1$ to illuminate the sample and to allow the detection of the fluorescent response $L_2$ by the detection unit 18. The output of the detection unit representative of data indicative of the detected light $L_2$ is received and processed by the utility $PD_1$ of the control unit 15 to display one or more images of the sample.

The present invention also facilitates the imaging of samples (e.g., biological samples) by providing a solution for another problem associated with the following. The substrate surface is typically located at an unknown distance from other structures of interest inside the cell or on its cytoplasmic membrane due to cell height. In research studies with the conventional techniques, this problem is handled by three-dimensional optical sectioning microscopy, acquiring a series of focal images that can start at the substrate and continue to the sample maximal height. However, such a 3D data acquisition of many "optical sections" is slow, taking many seconds even in fast systems, yielding a huge volume of digital data, and the processing time puts heavy burden on the computing power.

It appears that sufficiently good quantitative analyses, such as total fluorescence intensity evaluations and intracellular localization, can be obtained with the two dimensional projection of a three-dimensional structure. The reason for using three-dimensional image acquisition in the conventional systems (confocal or wide-field followed by deconvolution) is aimed at eliminating the complex out-of-focus contributions of high numerical aperture objectives.

The sweeping-focus technique of the present invention provides an alternative fast way for obtaining an image of the 2D projection of a 3D sample. In order to obtain the 2D-projection image of the 3D sample, the system 10 of FIG. 1 operates in the following manner. The focal plane of the objective 16 is initially located far below the substrate's surface $S_1$, while the shutter 19 in front of the light source 20 of the imaging channel is closed. The focal plane is continuously displaced towards the substrate. When the second intensity peak is detected (i.e., the sample-supporting surface $S_2$ of the substrate is in focus), the shutters 19 and 21 are opened, and the displacement of the focal plane along the Z-axis is continued, thereby enabling acquiring images of the sample integrating data over a range of heights within the specimen volume. Preferably, the shutter 19 should be opened somewhat prior to the detection of the second peak to enable recording out of focus contributions from regions outside the specimen volume. The time at which the shutter must be open (Δt) depends on the speed of the focal plane displacement ($v_f$) and the expected specimen height ($h_s$): $\Delta t = h_s/v_f$. The shutter is opened during the Z-scan of the sample's height and, preferably, a bit longer time to avoid losing information in both edges of the sample. The detection unit 18 integrates light coming from the sample during the continuous movement of the focal plane through the sample height along the optical axis of the objective. The so-measured image data is thus representative of the 2D projection of the 3D sample, but includes also the out-of-focus contributions. This data representation is received at the processing utility $PD_2$ where it undergoes two-dimensional deconvolution, resulting in the 2D-projection image of the sample. The results of this technique are comparable to the conventional technique (i.e., 3D deconvolution of a 3D representation followed by a 2D projection), and are obtainable with much higher image acquisition and post acquisition processing speeds.

The focal depth is inversely proportional to the numerical aperture NA of the focusing/collecting optics. In the extreme case, NA~0 (i.e., the focal depth is infinite), the image is a parallel beam projection, such as for Electron Microscopy. However, sub-cellular resolution light microscopy is inevitably associated with high numerical aperture imaging with very limited focal depth, as well as complex behavior of out-of-focus contributions. The contributions of out-of-focus patterns in an imaged sample cause loss of contrast (and effective resolution). Although confocal microscopes practically provide for reducing these contributions, the quantitative evaluation of the location and amount of labeled molecules in a biological sample is impeded by the intensity variations with distance from the focal plane, unless many, very closely spaced focal planes are acquired. This is not only slow and heavy on the computer, but also causes excessive bleach. Therefore, quantitative microscopy typically utilizes wide-field image acquisition where integrated intensities vary little from the in-focus image (just distributions are blurred). The sweeping focus acquisition maintains this feature, preserving the contributions of fluorescent labels throughout the sample volume.

Computational projection and 2D deconvolution of a focal series data was used for time-lapse data analysis (Hiraoka et al., Focal points for chromosome condensation and decondensation revealed by three-dimensional in vivo time-lapse microscopy, 1989, Nature 342, 293–296). With this technique, final results similar to those of 3D deconvolution followed by 2D projection technique were achieved, but at much greater speed and reduced load on computer storage and processing time. Here, the present invention also provides for dramatically cutting the image acquisition time, and enables high-throughput high-resolution microscopic screening of samples, such as light-microscopy for sub-cellular localization and quantification of fluorescently labeled molecules, notably, cells expressing inherently fluorescent proteins chimeric constructs.

The following is the description of the 2D-projection imaging technique utilized in the present invention. In this connection, it should be understood that convolution and projection are commutative linear operations, meaning that their order of activation can be exchanged without affecting the final result. A relation between a 3D microscope object $O^3(x,y,z)$ and an acquired 3D image thereof $M^3(x,y,z)$ is expressed by a 3D convolution as follows:

$$M^3(x, y, z) = \int\int\int dx'dy'dz'\, O^3(x', y', z') * P^3(x-x', y-y', z-z') \quad (1)$$
$$= O^3(x, y, z) \otimes^3 P^3(x, y, z)$$

wherein $P^3(x,y,z)$ is the convoluting kernel defined by the microscope 3D Point Spread Function (PSF), which is assumed to be independent of position (i.e., the so-called space variant); and $\otimes^3$ denotes a 3D convolution operation.

A 3D PSF is actually the 3D image of a point source resulted from imaging it at successive focal planes along the optical axis of the objective from $-\infty$ to $+\infty$, (practically for 100× objective, from 5 µm above the focal point to 5 µm below it). The z-projection of a 3D image is a 2D image given by the integral over z, and similar for the PSF and the object:

$$M^2(x,y)=\int dz\, M^3(x,y,z) \quad (2a)$$

$$P^2(x,y)=\int dz\, P^3(x,y,z) \quad (2b)$$

$$O^2(x,y)=\int dz\, O^3(x,y,z) \quad (2c)$$

Integration of the equation (1) along the z-axis gives:

$$M^2(x,y)=O^2(x,y) \otimes^2 P^2(x,y) \quad (3)$$

Equation (3) signifies that a measured sweeping focus image, $M^2(x,y)$, is related to the projection of the real 3D object, $O^2(x,y)$, by a 2D convolution, and the convolution kernel $P^2(x,y)$ is the z-projection of the microscope 3D PSF. It is therefore possible to invert this relation and use $P^2(x,y)$ in a 2D deconvolution that retrieves the projection from the sweeping focus measured presentation. Such a processing is commonly executed by iterative constraint deconvolution algorithms.

Figure 6A:
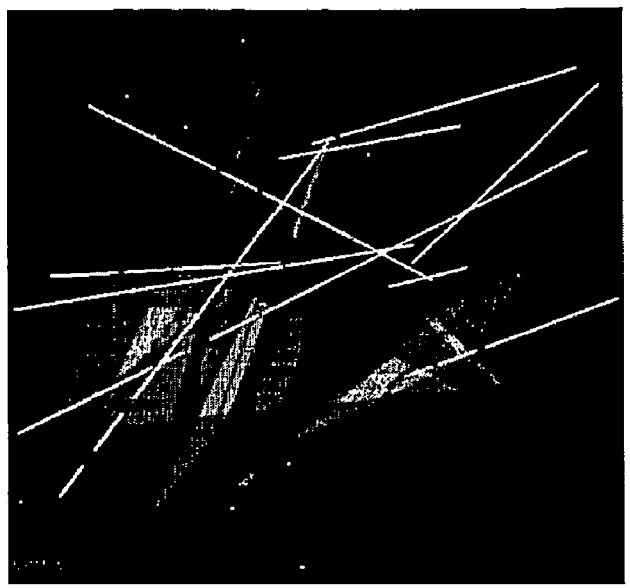
FIGS. 6A to 6C exemplify the results of simulating the invented technique using deconvolution for obtaining an image in the form of the two dimensional projection of a three-dimensional structure from the sweeping focus representation of the projection.
Figure 6B:
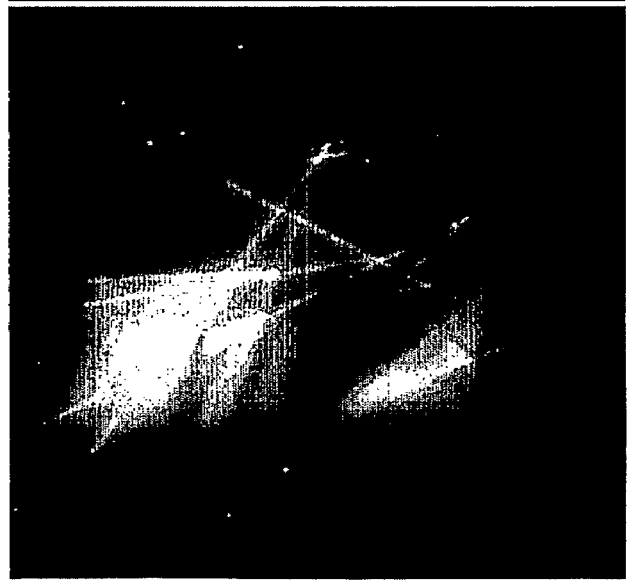
Figure 6C:

Reference is made to FIGS. 6A–6C showing the simulated results of obtaining the 2D-projection image of a simulated 3D structure composed of points, lines and triangular planes at random positions, heights and orientations. FIG. 6A illustrates a computed 2D-projection (z-projection) of the original 3D simulated image of this structure. FIG. 6B illustrates simulation of the sweeping-focus imaging of this structure, and presents a 2D-projection representation of the structure. This data representation was obtained by first convolving the 3D image with the microscope 3D PSF, and then projecting the convolution result along the Z-axis. As shown, the 2D data representation is in the form of a blurred image caused by the effects of the out-of-focus patterns of the structure. FIG. 6C illustrates the results of processing the 2D-projection representation of FIG. 6B by a 2D deconvolution. As shown, the blur is significantly reduced. The results of this technique (2D projection of FIG. 6C) are comparable to FIG. 6A, presenting the result achieved by the conventional 3D-image acquisition followed by a 3D deconvolution and projection along the Z-axis, other than the effect of the smear due to the resolution limit in-focus conditions. The 2D deconvoluted image actually presents the infinite depth-of-focus picture of a thick sample. The depth information within the sample is lost, but the fluorescence intensity is proportional to the number of fluorophores in the entire volume, and the sharpness of an object within the specimen volume approaches the lateral (X-Y) resolution defined by the in-focus conditions, independent of its Z-position. The information along the Z-axis can be retrieved by acquiring two sweeping focus images during translation of the sample stage in two opposite directions (±X), thereby creating a stereo-pair, as will be described further below.

Figure 7A:
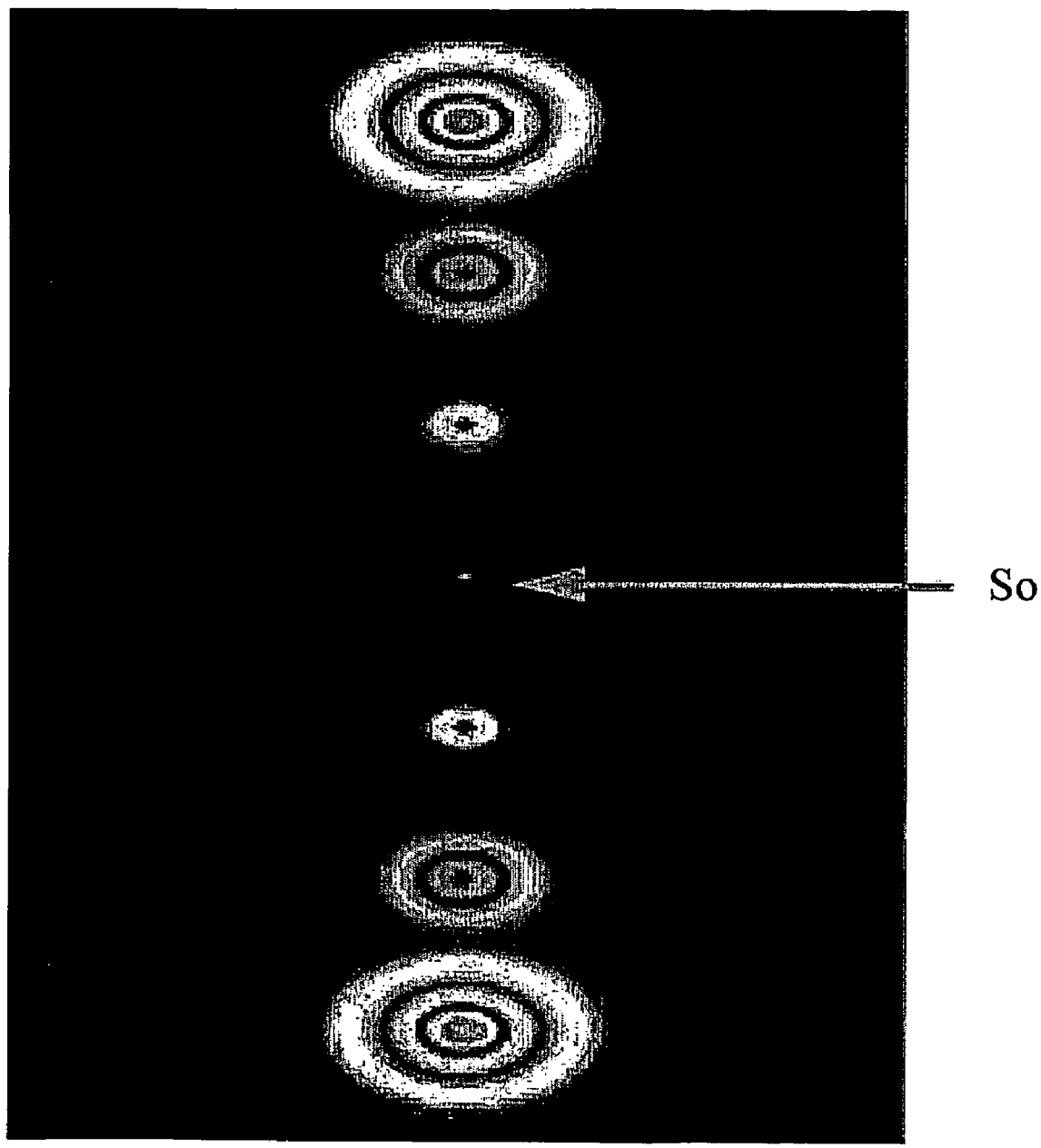
FIGS. 7A and 7B illustrate the theoretical results of calculating the 3D point spread function (PSF) of a microscope, and illustrate how the sweeping focus 2D PSF can be calculated from the 3D PSF.
Figure 7B:
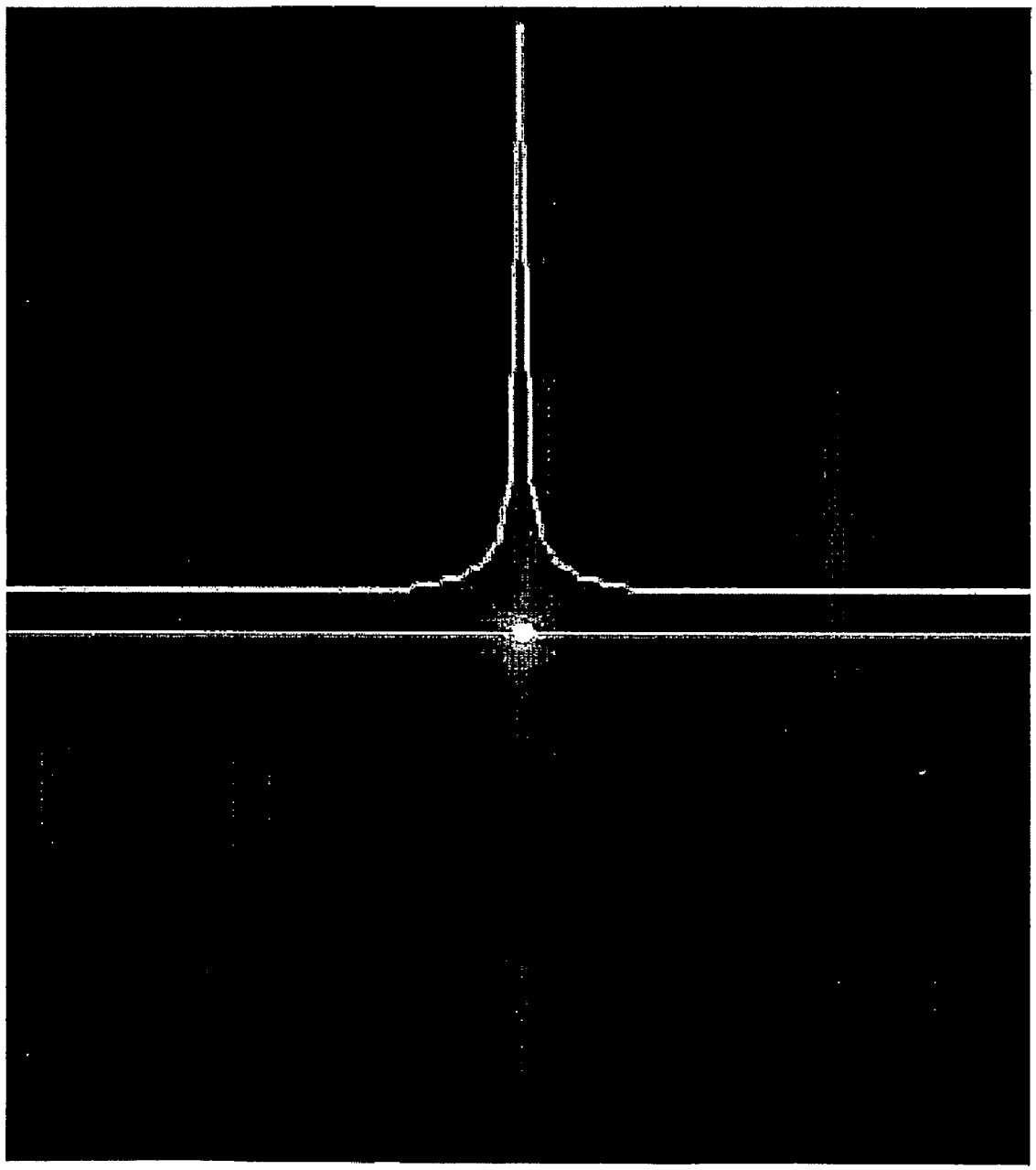

Reference is now made to FIGS. 7A and 7B showing how the 2D-sweeping focus PSF can be obtained experimentally and by calculations from theoretical models. Experimentally, sweeping focus images of sub-resolution sized fluorescent beads are simply acquired exactly as the sweeping-focus images are. Theoretically, any model for the microscope 3D PSF can be projected along the Z-axis. FIG. 7A shows a 3D image of a point source, i.e., PSF of the microscope, calculated according to the model of Stokseth (J. Opt. Soc. Am., 59, p. 1314–1321, 1969). The 3D image includes seven optical sections, a central one corresponding to the in-focus position of the point source, $S_0$, three optical sections above the focus, and three optical sections below the focus. At the in-focus position of the point source (plane Z=0), the image is in the form of a diffraction-limited point $S_0$. When the focal plane of the objective is displaced certain distances in two opposite Z-directions from the in-focus position of the source point, the image is blurred, displaying pronounced concentric ring structures (Airy rings). FIG. 7B illustrates the intensity profile of the 2D projection of the 3D image of FIG. 7A. (a line scan profile through the image center in FIG. 7B), showing how the intensity falls from its maximum at the center. The central point has roughly the same diffraction-limited diameter as the in-focus image, and is surrounded by decaying lobes, that totally averaged the ring structure (since it is continuously expanding as a function of distance from focus).

Figures 8A, 8B, 8C:
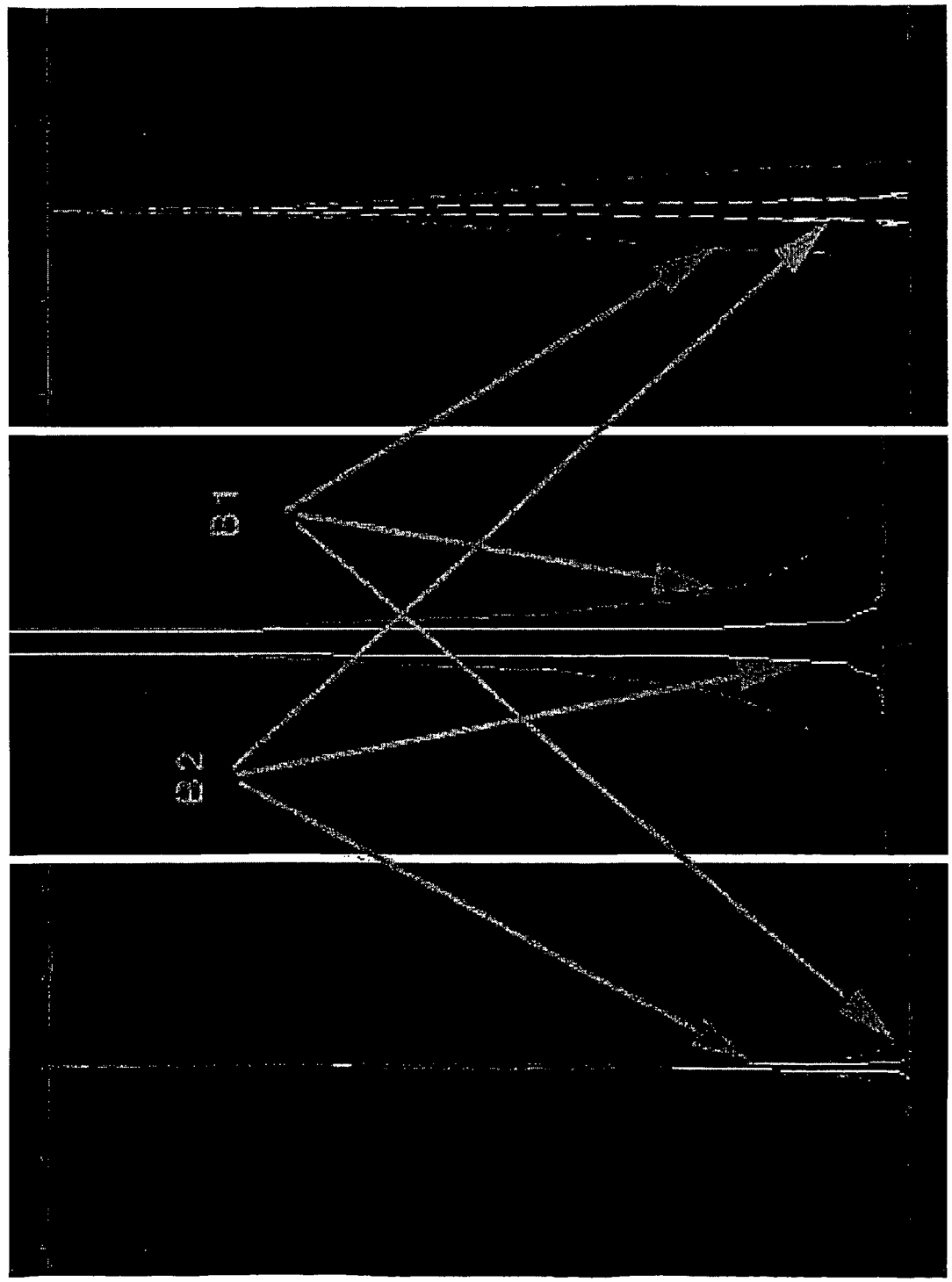
FIGS. 8A to 8C compare the light intensity profile of the sweeping focus image of the present invention (shown in FIG. 7B) to that of the in-focus image of a point like source.

FIGS. 8A to 8C compare the light intensity profile of the sweeping focus image of a point source obtained with the sweeping focus method of the present invention (graphs $B_1$) with that of the in-focus image of a point source (graphs $B_2$). FIG. 8A exemplifies the normalized line scan profile at the image center; FIG. 8B exemplifies the four-times magnified profile visualizing the out-of-focus contribution; and FIG. 8C shows the logarithmic scale of the same (three decimal decades).

Figures 9A, 9B:
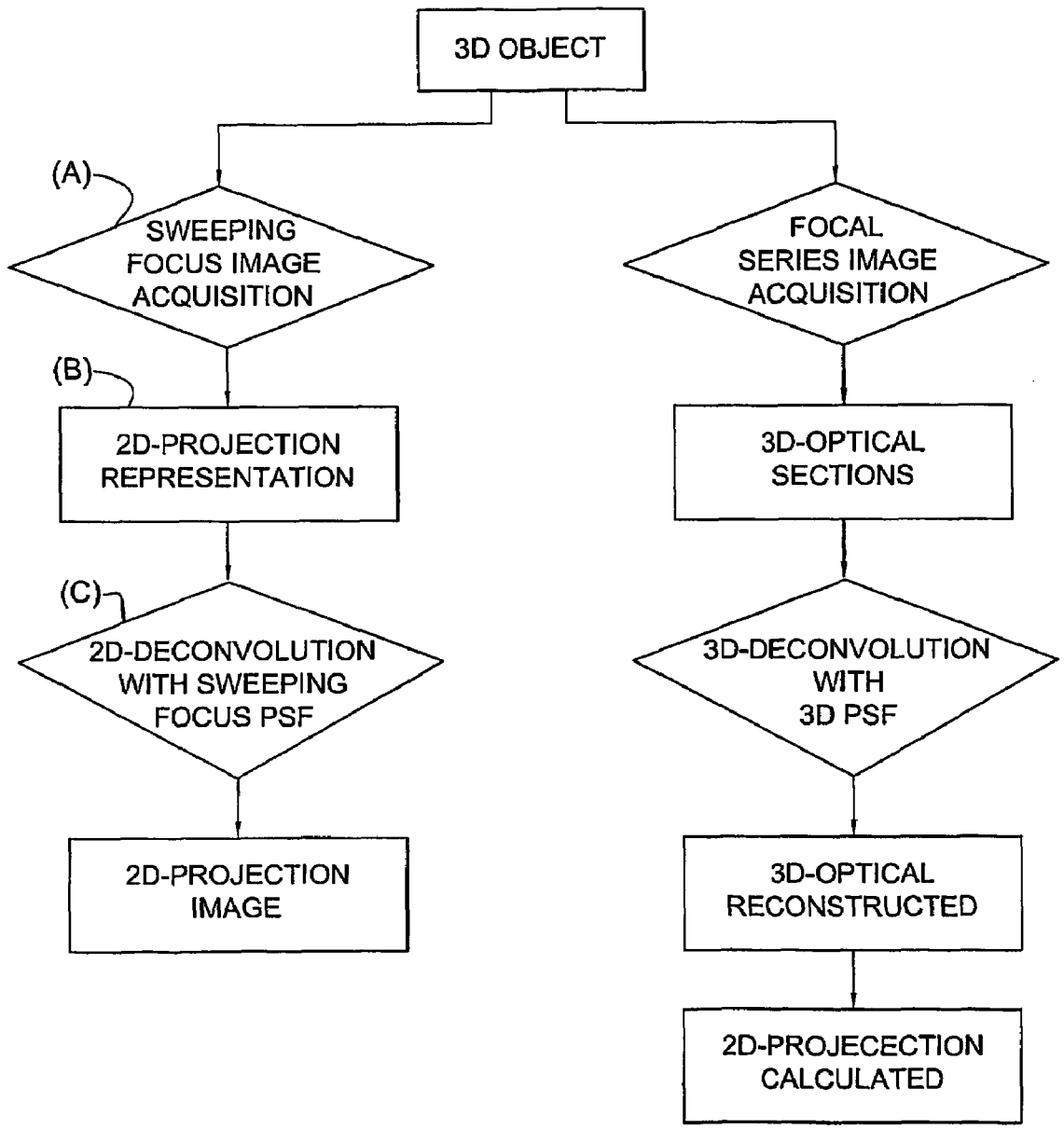
FIGS. 9A and 9B illustrate the main steps of the invented technique for obtaining the 2D-projection image of a 3D structure as compared to those of the conventional technique.

Referring to FIGS. 9A and 9B, there are illustrated the main operational steps of a method according to the invention for obtaining the 2D projection of a 3D object (FIG. 9A) as compared to that of the conventional technique (FIG. 9B). According to the invention (FIG. 9A), a sweeping focus image acquisition is applied to a 3D object (step A), thereby obtaining a 2D-projection representation (step B), which then undergoes a 2D deconvolution using sweeping focus PSF (step C) resulting in the 2D projection image. According to the conventional technique (FIG. 9B), a series of focal images of the 3D object are acquired resulting in a measured data in the form of a series of optical sections across the object Then, this measured data undergoes 3D deconvolution using a 3D-PSF, thereby reconstructing the 3D object and enabling the calculation of a 2D projection thereof.

Figure 10B:
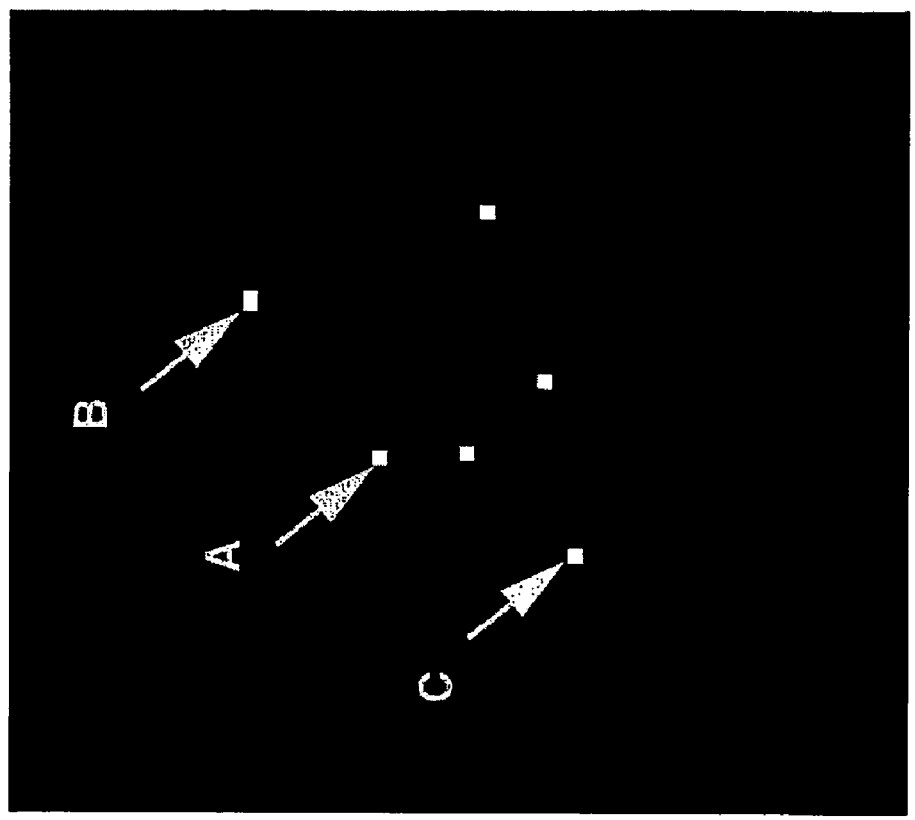
FIGS. 10A and 10B illustrate experimental results showing how the Z-information about the sample can be retrieved from two 2D-projection images of the sample simulating a stereo pair.
Figure 10A:
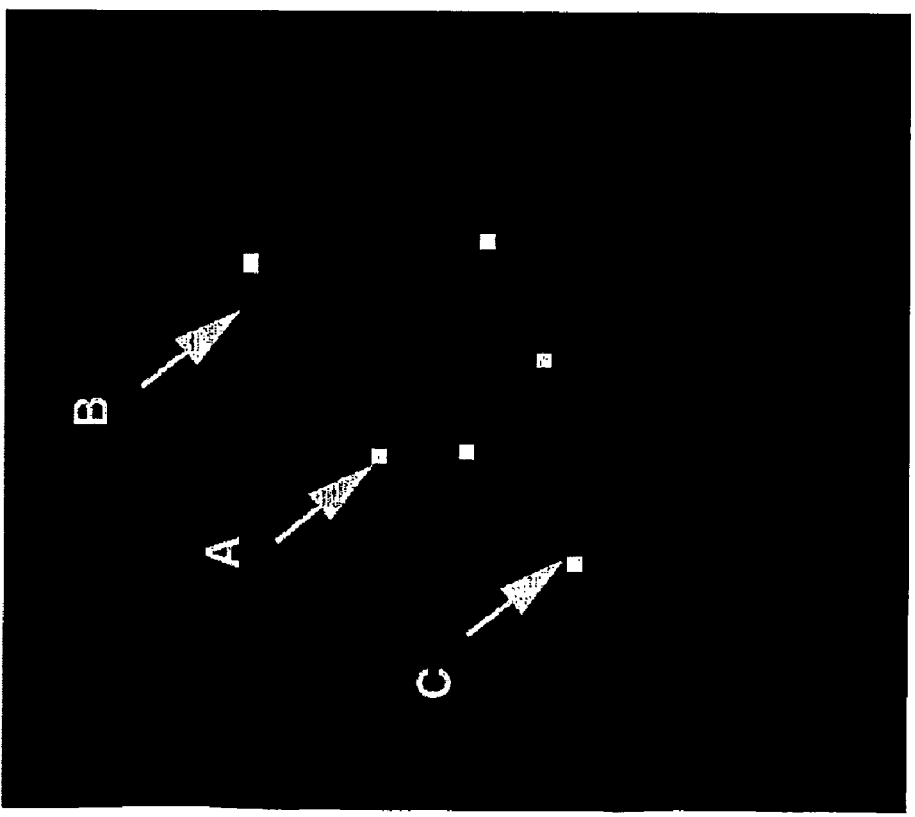

It should be understood that, for the purposes of the present invention, the 2D projection of the 3D-PSF, $P^2(x,y)$, should be measured or theoretically calculated (according to equation (2b) above) only once, for a given apparatus at a given configuration. Since data representative of a typical 2D image of a biological sample occupies about 2 Mbytes (in comparison to 100 Mbytes of that of a 3D image), the time saving in calculation is enormous. The trade off is loosing all the information about the z-component of the data, which can then be retrieved in the following manner:

FIGS. 10A and 10B show two 2D-projection images L and R, respectively, obtained by acquiring sweeping focus images of beads at different heights while translating the microscope stage (substrate S in FIG. 1) in two opposite (±x) directions, thereby creating a stereo-pair. The ratio between the Z- and X-speeds of translation is defined as F. The two images are then processed by deconvolution. Strictly speaking, such sweeping of focus together with shifting X-position has its special 2D PSF functions (easily calculated from the 3D PSF by the projection at an axis tilted with respect to the Z-axis). The results, however, are sufficiently close to the untilted projection, which can be used as an excellent approximation. An algorithm of reconstructing the Z-position of continuous objects from stereo pairs of electron micrographs has been developed (Cheng, Y, Hartemink C. A., Hartwig, J. H. Forbes Dewey Jr. C., Three-dimensional reconstruction of the actin cytoskeleton from stereo images. J. Biomechanics, 33, p. 105–113, 2000). Defining the Z-position of highly localized labeled spots is particularly simple, since a relative shift in position from image L to image R is proportional to the height: In the image L, points A, B and C are shown, which signify the following: point A is the reference bead (i.e., Z=0 corresponding to the in-focus position of the bead's plane); point B is a bead that shifts $(-x_1)$ between the images L and R, therefore being at "height" of $(-x_1 \cdot F)=(-Z_1)$; point C presents a smaller $(+x_2)$ shift between the images L and R, the "height" of the point C therefore being $(x_2 \cdot F)=Z_2$.

The post-acquisition, computational method of obtaining the 2D-projection image of a 3D object by 3D acquisition, projection, and then 2D deconvolution (e.g., from the above indicated article of Hiraoka et al), is implemented in the present invention by hardware, using the sweeping focus method. This serves for saving the time needed for acquisition and processing of a large number of images (e.g., 64 section images). In the invention, based on equation (3) above, the 2D deconvolution (step C in FIG. 9A) is preferably based on iterative constrained deconvolution (Agard D. A. and Sedat, J. W. (1983) Nature 302, 676–681; Agard D. A., Optical sectioning microscopy: cellular architecture in three dimensions, Ann. Rev. Biophys. Bioeng., 13, p. 191–219, 1984; Swedlow J. R., Sedat J. W., Agard D. A. in: Jansson, P. A. editor, Deconvolution of images and spectra, Academic Press NY, chapter 9, pp. 284–309, 1997), which is conveniently computed in the Fourier space, and avoids dividing by small values. The convolution of two 2D functions (indicative of the object and the sweeping focus 2D PSF) has algorithmic complexity of the order of $N^4$, N being the number of pixels in one dimension, while in the Fourier space, the procedure (using Fast Fourier Transform) is of complexity of $N^2\ln(N^2 \sim N^2(\ln N)$ only. Therefore, the Fourier transforms of equation (3) can be carried out, wherein the convolution in the real space is replaced by multiplication in Fourier space. At each iteration, a guess image is convoluted with the PSF, compared to the measured sweeping focus presentation, and the deviations are used to correct the guess, assure its positivity, and continue to next iteration.

The following are examples of experimental results of the technique of the present invention. 3D focal series and sweeping focus 2D projection images were acquired from fluorescently labeled specimens. 3D constrained deconvolutions were calculated (Agard D. A., Optical sectioning microscopy: cellular architecture in three dimensions, Ann. Rev. Biophys. Bioeng., 13, p. 191–219, 1984; Swedlow J. R., Sedat J. W., Agard D. A. in: Jansson, P. A. editor, Deconvolution of images and spectra, Academic Press NY, chapter 9, pp. 284–309, 1997). Then, deconvoluted 3D result was processed by computed projection, and compared to the sweeping focus acquired image of the same samples followed by 2D deconvolution with the sweeping focus PSF. This is illustrated in FIGS. 11A to 11G. FIGS. 11A and 11B illustrate sweeping focus images before and after deconvolution, respectively, for a mitochondria. FIG. 11C is the 3D deconvoluted and projected corresponding image. FIGS. 11D and 11E illustrate sweeping focus images before and after deconvolution, respectively, for a muscle cell sample. FIG. 11F is the 3D deconvolved and projected respective image, and FIG. 11G is the enlarged view of the image of FIG. 11F.

Those skilled in the art will readily appreciate that various modifications and changes can be applied to the embodiment of the invention as hereinbefore exemplified without departing from its scope defined in and by the appended claims. It should be understood that, although the present invention is described herein with respect to a specific example of imaging biological samples, the technique of the present invention can be used for inspecting samples of other types, provided a sample under inspection is located in a plate-like substrate transparent with respect to predetermined incident radiation. Considering the entire imaging system (10 in FIG. 1), it should be understood that for samples other than those having fluorescent labels, imaging and auto-focusing channels could utilize the same light source, and therefore a light directing assembly would be simpler.

The invention claimed is:

1. An auto-focusing method for determining an in-focus position of a sample supported on one surface of a substrate plate made of a material transparent with respect to incident electromagnetic radiation, the method utilizing an optical system capable of directing incident electromagnetic radiation towards the sample and collecting reflections of the incident electromagnetic radiation which are to be detected, and comprising:
   (i) locating a focal plane of an objective lens arrangement at a predetermined distance from a surface of the substrate, which is opposite to said surface supporting the sample;
   (ii) providing continuous displacement of the focal plane relative to the substrate along the optical axis of the objective lens arrangement, while concurrently directing the incident radiation towards the sample through the objective lens arrangement to thereby focus the incident radiation to a location at the focal plane of the objective lens arrangement; and
   (iii) continuously detecting reflected components of the electromagnetic radiation collected through said objective lens arrangement, said detected reflected components being characterized by a first intensity peak corresponding to an in-focus position of said opposite surface of the substrate, and a second intensity peak spaced in time from the first intensity peak and corresponding to an in-focus position of said sample-supporting surface of the substrate, thereby enabling imaging of the sample when in the in-focus nposition of the sample-supporting surface of the substrate.

2. The method according to claim 1, wherein said incident radiation is in a spectral range incapable of causing luminescent response of the sample having luminescent labels therein.

3. The method according to claim 2, wherein said imaging comprises irradiating the sample having luminescent labels by incident electromagnetic radiation of a wavelength range capable of exciting a luminescent response of the sample, detecting said luminescent response by an imaging detector, and generating data indicative thereof.

4. The method according to claim 3, wherein said incident exciting radiation is directed to the sample and the luminescent response is directed to the imaging detector, through said objective lens arrangement.

5. The method according to claim 4, further comprising spatially separating the luminescent response and the reflected components to allow detection of the luminescent response of the sample by said imaging detector and prevent the reflected components from reaching the imaging detector.

6. The method according to claim 1, wherein said displacement is started from a certain distance between the focal plane and said opposite surface of the substrate.

7. The method according to claim 1, wherein the displacement of the focal plane is slowed upon detecting said first intensity peak.

8. The method according to claim 1, comprising providing a relative displacement between the optical axis of the objective lens arrangement and the substrate in a plane perpendicular to said optical axis, to thereby provide intersection of the optical axis with successive locations of the substrate in said plane, and repeating steps (ii) and (iii) with respect to the successive locations of the substrate.

9. The method according to claim 1, wherein a numerical aperture of the incident beam propagation towards the objective lens arrangement is such as to fill a back aperture defined by the objective lens arrangement.

10. The method according to claim 1, comprising spatially separating the incident and reflected radiation components, to allow detection of the reflected radiation.

11. The method according to claim 1, comprising passing the collected reflected radiation, propagating towards a detector, through a pinhole, thereby filtering out radiation components reflected from out-of-focus locations and sharpening the detected intensity peak corresponding to the light components reflected from the in-focus locations.

12. The method according to claim 1, comprising imaging the sample when in the in-focus position of the sample-supporting surface of the substrate.

13. The method according to claim 1, further comprising:
   performing a sweeping-focus acquisition mode continuously acquiring images of successive planes of the three-dimensional sample along the optical axis of the objective lens arrangement, by continuously displacing the focal plane of the objective lens arrangement through the sample, starting at the sample-supporting surface of the substrate, thereby obtaining data representation of the two-dimensional projection of the three-dimensional sample onto a two-dimensional pixel array of a detector;
   processing said data representation by carrying out a two-dimensional deconvolution thereof with a predetermined Point Spread Function of a sweeping-focusing acquisition mode, thereby obtaining a deblurred image of the two-dimensional projection of the three-dimensional sample.

14. The method according to claim 13, wherein the sweeping focus acquisition mode comprises continuously irradiating the sample having luminescent labels therein with incident exciting radiation causing luminescent response of the sample, and continuously detecting the luminescent responses coming from the successive planes of the sample.

15. A method for obtaining an image of a three-dimensional sample in the form of a two-dimensional projection of the sample, which is supported on a substrate plate made of a material transparent for incident radiation, the method comprising:
   (a) applying to the sample on substrate the auto-focusing method of claim 1 thereby obtaining data representative of a two-dimensional projection of images of successive planes of the sample along the optical axis of the objective lens arrangement, which are continuously acquired by a two-dimensional pixel array of a detector during the relative displacement between the focal plane of the objective lens arrangement and the sample along the optical axis of the objective lens arrangement through the sample;
   (b) processing said data by carrying out a two-dimensional deconvolution thereof with the predetermined Point Spread Function of an imaging system, thereby obtaining said image in the form of the two-dimensional projection of the three-dimensional sample.

16. An auto-focusing device for determining an in-focus position of a sample supported on a surface of a substrate plate made of a material transparent with respect to incident electromagnetic radiation, the device comprising:
   a light source generating a beam of the incident radiation of a predetermined wavelength range;
   a focusing optics including an objective lens arrangement;
   a light directing assembly, which is operable for directing the incident beam towards the sample through the objective lens arrangement with a predetermined numerical aperture of beam propagation to irradiate a location on a focal plane of the objective lens arrangement, and for directing reflections of said incident radiation collected by said objective lens arrangement to a detector unit, which is operable to detect said reflections and generate data indicative of their intensities;

a drive assembly operable to provide continuous relative displacement between the focal plane of said objective lens arrangement and the substrate along the optical axis of the objective lens arrangement; and a control unit for operating said drive assembly to provide said continuous relative displacement and instantaneous stop of the displacement, for operating said light source and said detector to allow continuous detection of said reflections during the displacement of the focal plane, said control unit comprising a processing device operable to be responsive to said data generated by the detector unit to identify a first intensity peak corresponding to the in-focus position of a surface of said substrate opposite to the sample-supporting surface of the substrate, and identify a second intensity peak spaced in time from the first intensity peak and corresponding to the in-focus position of the sample-supporting surface of the substrate, and to generate an auto-focusing signal upon detecting said second intensity peak.

17. The device according to claim 16, wherein said predetermined wavelength range of the incident radiation is incapable of causing luminescent response of the sample having luminescent labels therein.

18. The device according to claim 16, wherein said light directing assembly comprises a beam splitter for spatially separating between the incident and reflected radiation components, and allowing propagation of the reflected radiation components towards the detection unit.

19. The device according to claim 16, wherein the light directing assembly comprises a beam expander for providing said predetermined numerical apertures of the incident beam propagation to fill a back aperture defined by the objective lens arrangement.

20. The device according to claim 16, wherein said detection unit comprises a pinhole accommodated in the path of the collected reflected radiation propagating to a detector.

21. The device according to claim 16, wherein said control unit is operable to slow the displacement of the focal plane, upon detecting said first intensity peak.

22. The device according to claim 16, wherein said control unit is operable to actuate an image acquisition mode to acquire images of the sample when in the in-focus position of the sample-supporting surface of the substrate.

23. The device according to claim 22, wherein the control unit is connectable to an imaging device operable to carry out said image acquisition mode.

24. The device according to claim 16, wherein said control unit is operable to actuate the drive assembly to provide a continuous displacement of the focal plane relative to the substrate through successive planes of the substrate along the optical axis of the objective lens arrangement starting from the sample-carrying surface, and to actuate an image acquisition mode to continuously acquire images of the successive planes of the sample.

25. The device according to claim 24, comprising a processing device for processing data indicative of said images to obtain a two-dimensional projection of the three-dimensional sample.

26. An imaging system comprising the auto-focusing device of claim 16, and an imaging device utilizing said objective lens arrangement and defining an imaging channel for electromagnetic radiation propagation towards and away from the objective lens arrangement separated from the auto-focusing channel defined by the auto-focusing device, said imaging device comprising a light source generating incident radiation and an imaging detection unit.

27. The system according to claim 26, wherein said predetermined wavelength range of the incident radiation used in the auto-focusing device is incapable of causing luminescent response of the sample having luminescent labels therein, said imaging device comprising a light source generating incident exciting radiation to excite a luminescent response of the sample, said response being collected by the objective lens arrangement and directed to the imaging detection unit.

28. The system according to claim 27, comprising a wavelength selective beam splitter accommodated in the paths of the collected reflected radiation and the collected luminescent response to provide said spatial separation between the radiation components propagating through the imaging and auto-focusing channels.

* * * * *

UNITED STATES PATENT AND TRADEMARK OFFICE
CERTIFICATE OF CORRECTION

PATENT NO. : 7,109,459 B2
APPLICATION NO. : 10/506860
DATED : September 19, 2006
INVENTOR(S) : Kam et al.

It is certified that error appears in the above-identified patent and that said Letters Patent is hereby corrected as shown below:

Column 2, Line 11,
Please delete "confocal microscope"
and
replace with
-- U.S. Pat. Nos. 5,783,814 and 5,672,861 describe focusing in a confocal microscope --

Signed and Sealed this

Twenty-eighth Day of August, 2007

JON W. DUDAS
*Director of the United States Patent and Trademark Office*